(12) United States Patent
Wilford et al.

(10) Patent No.: US 7,144,413 B2
(45) Date of Patent: Dec. 5, 2006

(54) GRAFT FIXATION SYSTEM AND METHOD

(75) Inventors: Troy Wilford, Malvern, PA (US); Cory W. Carter, Wilmington, DE (US)

(73) Assignee: Synthes (U.S.A.), West Chester, PA (US)

( * ) Notice: Subject to any disclaimer, the term of this patent is extended or adjusted under 35 U.S.C. 154(b) by 77 days.

(21) Appl. No.: 09/839,562

(22) Filed: Apr. 20, 2001

(65) Prior Publication Data

US 2002/0156476 A1 Oct. 24, 2002

(51) Int. Cl.
*A61B 17/04* (2006.01)
*A61F 2/08* (2006.01)

(52) U.S. Cl. .................. 606/232; 623/13.11

(58) Field of Classification Search .......... 606/73, 606/72, 53, 232; 623/13, 11.11, 13.14
See application file for complete search history.

(56) References Cited

U.S. PATENT DOCUMENTS

| | | | |
|---|---|---|---|
| 2,696,817 A | 12/1954 | Prevo | 128/92 |
| 3,065,660 A | 11/1962 | Puterbaugh | 85/5 |
| 3,170,270 A | 2/1965 | Sparber et al. | 50/313 |
| 3,260,149 A | 7/1966 | Deaver | 85/1 |
| 3,386,138 A | 6/1968 | Overman | 24/211 |
| 3,499,222 A | 3/1970 | Linkow et al. | 32/2 |
| 3,528,466 A | 9/1970 | Tracy | 144/32 |
| 4,030,503 A | 6/1977 | Clark, III | 128/304 |
| 4,301,551 A | 11/1981 | Dore et al. | 3/1 |
| 4,307,473 A | 12/1981 | Weber | 3/1.91 |
| 4,318,651 A | 3/1982 | Ragen | 411/342 |
| 4,463,753 A | 8/1984 | Gustilo | 128/92 |
| 4,616,455 A | 10/1986 | Hewison | 52/127.12 |
| 4,640,271 A | 2/1987 | Lower | 128/92 YF |
| 4,644,957 A | 2/1987 | Ricciardelli et al. | 128/642 |

(Continued)

FOREIGN PATENT DOCUMENTS

CH 669898 4/1989

(Continued)

*Primary Examiner*—Teena Mitchell
(74) *Attorney, Agent, or Firm*—Jones Day

(57) ABSTRACT

A graft fixation device, system and method are disclosed for reconstruction or replacement of a ligament or tendon preferably wherein a soft tissue graft or a bone-tendon-bone graft is received and implanted in a bone tunnel. The graft fixation system includes a fixation device comprising a threaded body which is rotatably connected to a graft interface member. One embodiment of the implant/graft interface member includes an enclosed loop for holding a soft tissue graft. Another embodiment of the interface member includes a bone cage comprising a cage bottom and removable cage top to hold a bone block at one end of a bone-tendon-bone (BTB) graft. An additional embodiment of the interface member includes a one-piece bone cage which may be crimped or stapled to a bone block. The fixation device holds a graft in centered axial alignment in a bone tunnel. The body portion of the fixation device may be turned without imparting substantial twist to a graft attached to the device, due to the rotatable coupling between the threaded body and the interface member. The fixation device may be installed using a driver tool that has a shaft and an outer sleeve, wherein the driver may be used to twist the fixation device and independently exert a pushing or pulling force thereto. The graft fixation method may be used to install a fixation device by pulling or pushing it into a prepared bone tunnel while minimizing the possibility of abrasion or other damage to a graft attached to the fixation device.

24 Claims, 19 Drawing Sheets

U.S. PATENT DOCUMENTS

| | | | |
|---|---|---|---|
| 4,694,544 A | 9/1987 | Chapman | 24/625 |
| 4,762,453 A | 8/1988 | DeCaro | 411/383 |
| 4,858,601 A | 8/1989 | Glisson | 128/92 R |
| 4,870,957 A | 10/1989 | Goble et al. | 128/92 |
| 4,887,385 A | 12/1989 | James et al. | 47/41.12 |
| 4,917,554 A | 4/1990 | Bronn | 411/392 |
| 4,947,502 A | 8/1990 | Engelhardt | 10/10 R |
| RE33,348 E | 9/1990 | Lower | 606/65 |
| 4,955,916 A | 9/1990 | Carignan et al. | 623/21 |
| 5,014,390 A | 5/1991 | De Gastines | 16/4 |
| 5,090,857 A * | 2/1992 | Dunn | 411/385 |
| 5,098,434 A | 3/1992 | Serbousek | 606/73 |
| 5,102,414 A | 4/1992 | Kirsch | 606/73 |
| 5,108,433 A | 4/1992 | May et al. | 623/13 |
| 5,122,133 A | 6/1992 | Evans | 606/73 |
| 5,129,902 A | 7/1992 | Goble et al. | 606/65 |
| 5,151,104 A | 9/1992 | Kenna | 606/73 |
| 5,152,790 A | 10/1992 | Rosenberg et al. | 623/13 |
| 5,169,400 A | 12/1992 | Mühling et al. | 606/73 |
| 5,203,787 A | 4/1993 | Noblitt et al. | 606/232 |
| 5,211,647 A | 5/1993 | Schmieding | 606/104 |
| 5,234,430 A | 8/1993 | Huebner | 606/60 |
| 5,258,000 A | 11/1993 | Gianturco | 606/151 |
| 5,268,001 A | 12/1993 | Nicholson et al. | 606/72 |
| 5,356,424 A | 10/1994 | Buzerak et al. | 606/223 |
| 5,360,431 A | 11/1994 | Puno et al. | 606/72 |
| 5,382,260 A | 1/1995 | Dormandy, Jr. et al. | 606/151 |
| 5,397,356 A | 3/1995 | Goble et al. | 623/13 |
| 5,407,427 A | 4/1995 | Zhu et al. | 604/26 |
| 5,417,692 A | 5/1995 | Goble et al. | 606/73 |
| 5,443,467 A | 8/1995 | Biedermann et al. | 606/65 |
| 5,443,509 A | 8/1995 | Boucher et al. | 623/16 |
| 5,454,811 A | 10/1995 | Huebner | 606/60 |
| 5,456,685 A | 10/1995 | Huebner | 606/73 |
| 5,464,427 A | 11/1995 | Curtis et al. | 606/232 |
| 5,470,334 A | 11/1995 | Ross et al. | 606/72 |
| 5,476,464 A | 12/1995 | Metz-Stavenhagen et al. | 606/61 |
| 5,496,326 A * | 3/1996 | Johnson | 606/88 |
| 5,507,822 A | 4/1996 | Bouchon et al. | 623/21 |
| 5,531,763 A | 7/1996 | Mastri et al. | 606/148 |
| 5,536,274 A | 7/1996 | Neuss | 623/1 |
| 5,549,608 A | 8/1996 | Errico et al. | 606/61 |
| 5,582,616 A | 12/1996 | Bolduc et al. | 606/143 |
| 5,584,629 A | 12/1996 | Bailey et al. | 411/178 |
| 5,584,835 A | 12/1996 | Greenfield | 606/73 |
| 5,591,166 A | 1/1997 | Bernhardt et al. | 606/61 |
| 5,601,558 A | 2/1997 | Torrie et al. | 606/72 |
| 5,613,968 A | 3/1997 | Lin | 606/61 |
| 5,626,613 A | 5/1997 | Schmieding | 606/232 |
| 5,632,748 A | 5/1997 | Beck, Jr. et al. | 606/89 |
| 5,634,754 A | 6/1997 | Weddendorf | 411/354 |
| 5,643,266 A | 7/1997 | Li | 606/72 |
| 5,643,267 A | 7/1997 | Hitomi et al. | 606/73 |
| 5,645,547 A | 7/1997 | Coleman | 606/73 |
| 5,649,926 A | 7/1997 | Howland | 606/61 |
| 5,662,683 A | 9/1997 | Kay | 606/232 |
| 5,728,116 A | 3/1998 | Rosenman | 606/151 |
| 5,741,256 A | 4/1998 | Bresina | 606/62 |
| 5,743,912 A | 4/1998 | Lahille et al. | 606/65 |
| 5,752,955 A | 5/1998 | Errico | 606/61 |
| 5,766,250 A | 6/1998 | Chervitz et al. | 623/13 |
| 5,782,844 A | 7/1998 | Yoon et al. | 606/139 |
| 5,782,865 A | 7/1998 | Grotz | 606/232 |
| 5,810,818 A | 9/1998 | Errico et al. | 606/61 |
| 5,827,285 A | 10/1998 | Bramlet | 606/60 |
| 5,849,004 A | 12/1998 | Bramlet | 606/232 |
| 5,871,504 A | 2/1999 | Eaton et al. | 606/232 |
| 5,895,398 A | 4/1999 | Wensel et al. | 606/159 |
| 5,895,425 A | 4/1999 | Grafton et al. | 623/16 |
| 5,899,902 A | 5/1999 | Brown et al. | 606/61 |
| 5,902,303 A | 5/1999 | Eckhof et al. | 606/60 |
| 5,904,696 A | 5/1999 | Rosenman | 606/151 |
| 5,911,721 A | 6/1999 | Nicholson et al. | 606/72 |
| 5,921,982 A | 7/1999 | Lesh et al. | 606/41 |
| 5,931,840 A * | 8/1999 | Goble et al. | 606/73 |
| 5,935,129 A | 8/1999 | McDevitt et al. | 606/72 |
| 5,957,953 A | 9/1999 | DiPoto et al. | 606/232 |
| 5,961,524 A | 10/1999 | Crombie | 606/104 |
| 5,964,764 A | 10/1999 | West, Jr. et al. | 606/72 |
| 5,968,045 A | 10/1999 | Frazier | 606/73 |
| 5,968,078 A | 10/1999 | Grotz | 606/232 |
| 5,971,987 A | 10/1999 | Huxel et al. | 606/73 |
| 5,980,524 A | 11/1999 | Justin et al. | 606/75 |
| 5,989,255 A | 11/1999 | Pepper et al. | 606/73 |
| 6,001,100 A | 12/1999 | Sherman et al. | 606/72 |
| 6,010,503 A | 1/2000 | Richelsoph et al. | 606/61 |
| 6,027,523 A | 2/2000 | Schmieding | 606/232 |
| 6,036,694 A | 3/2000 | Goble et al. | 606/72 |
| 6,036,701 A | 3/2000 | Rosenman | 606/151 |
| 6,048,344 A | 4/2000 | Schenk | 606/73 |
| 6,056,752 A | 5/2000 | Roger | 606/72 |
| 6,117,162 A | 9/2000 | Schmieding et al. | 606/232 |
| 6,117,173 A | 9/2000 | Taddia et al. | 623/16.11 |
| 6,129,763 A * | 10/2000 | Chauvin et al. | 623/17.11 |
| 6,139,565 A | 10/2000 | Stone et al. | 606/232 |
| 6,159,235 A | 12/2000 | Kim | 606/232 |
| 6,159,244 A * | 12/2000 | Suddaby | 623/17.11 |
| 6,214,007 B1 * | 4/2001 | Anderson | 606/73 |
| 6,221,107 B1 * | 4/2001 | Steiner et al. | 623/13.14 |
| 6,302,886 B1 | 10/2001 | McDevitt et al. | 606/72 |
| 6,387,129 B1 * | 5/2002 | Rieser et al. | 623/13.14 |
| 6,517,542 B1 * | 2/2003 | Papay et al. | 606/73 |

FOREIGN PATENT DOCUMENTS

| | | |
|---|---|---|
| DE | 824377 | 7/1949 |
| DE | 19529901 | 2/1996 |
| EP | 298400 | 1/1989 |
| EP | 374088 | 6/1990 |
| FR | 2678507 | 1/1993 |
| JP | 8066410 | 3/1993 |
| JP | 5300917 | 11/1996 |
| JP | 10155820 | 6/1998 |
| RU | 2008940 | 3/1994 |
| SU | 860758 | 7/1981 |
| SU | 1105193 | 7/1984 |
| SU | 1237191 | 6/1986 |

* cited by examiner

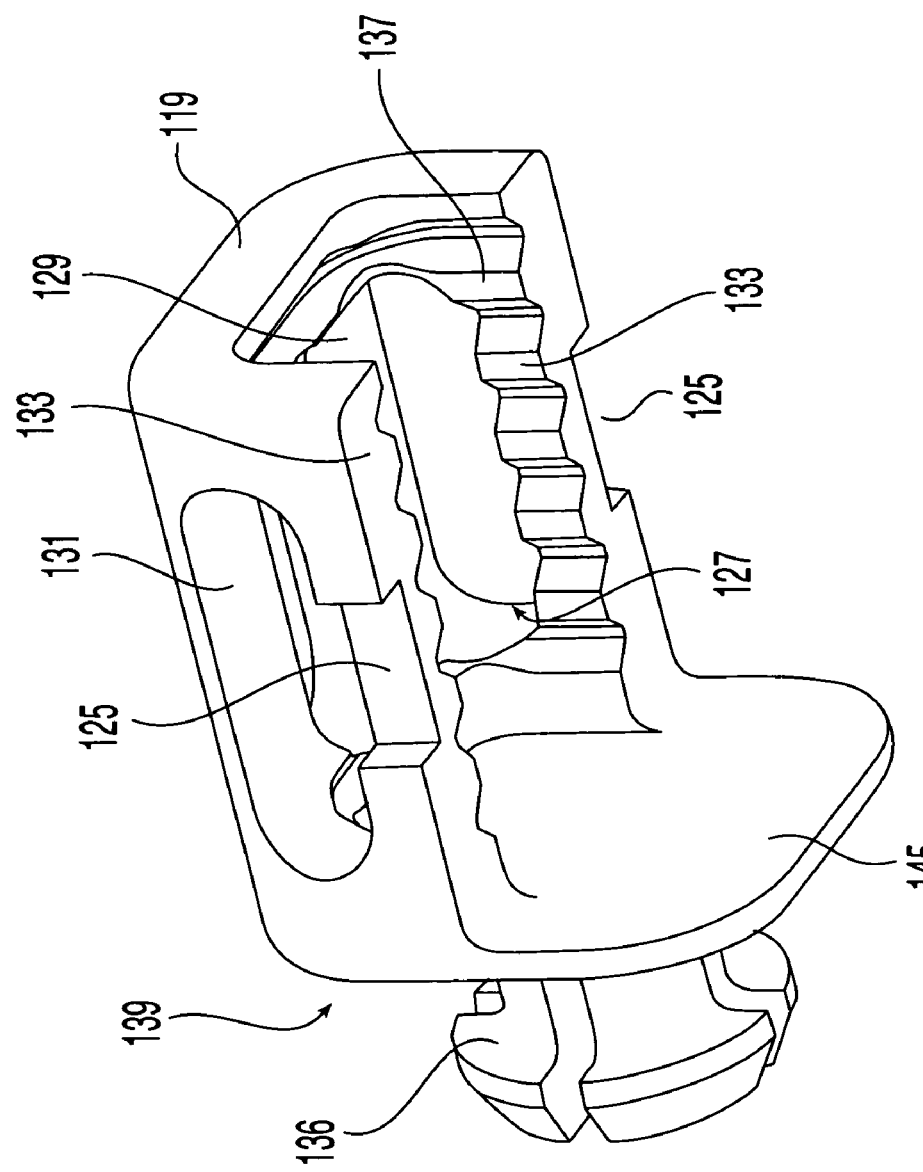

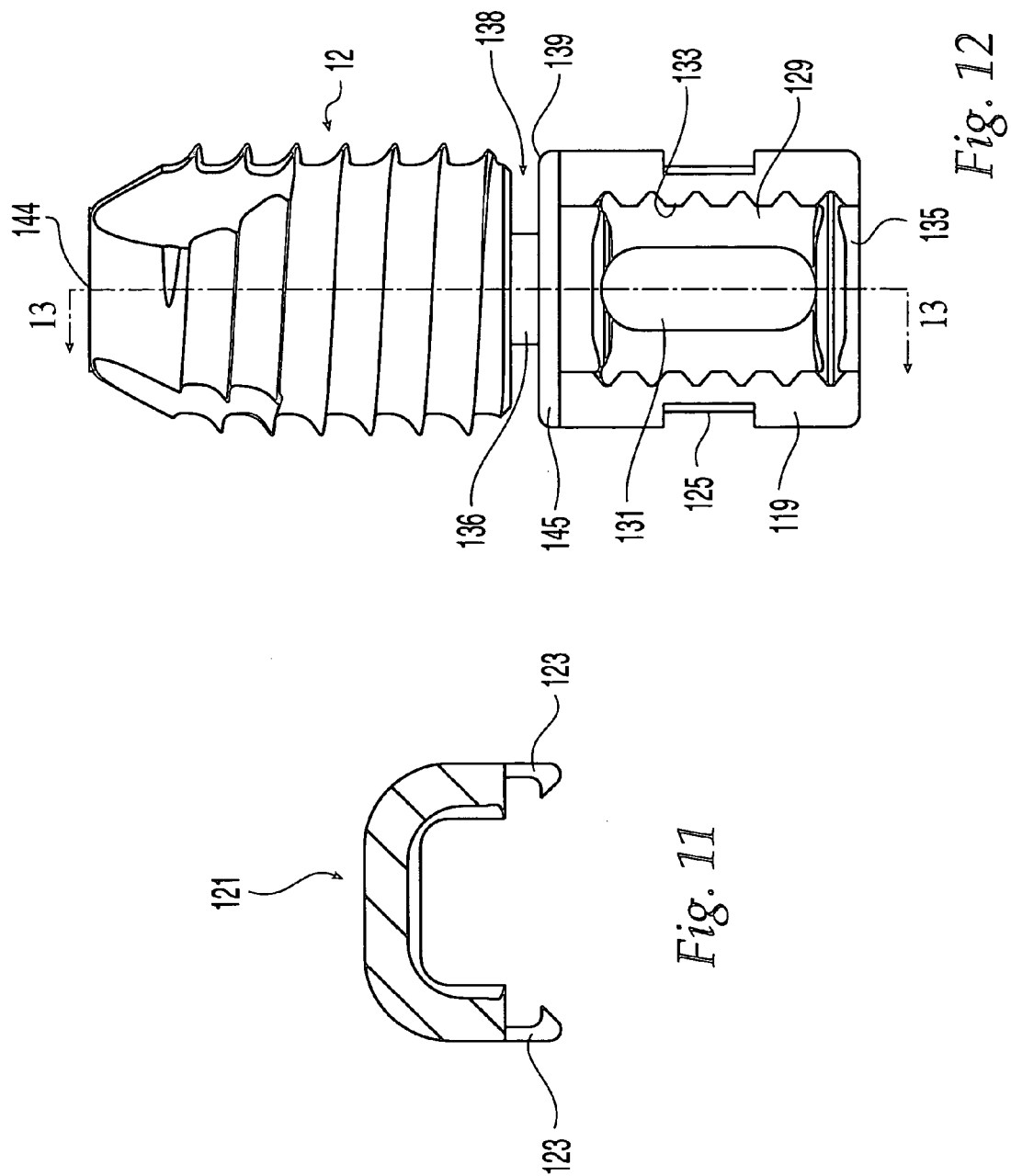

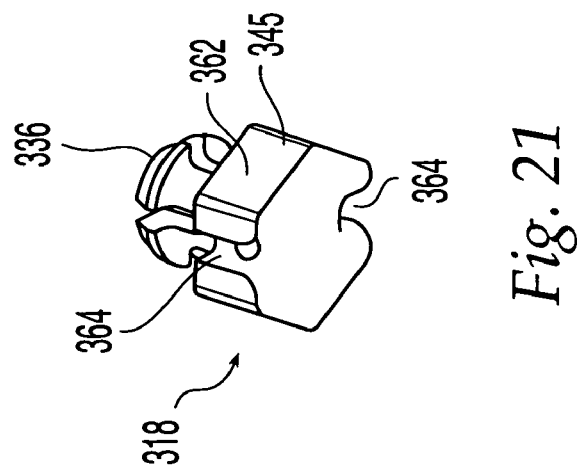
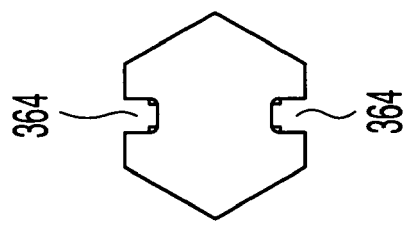
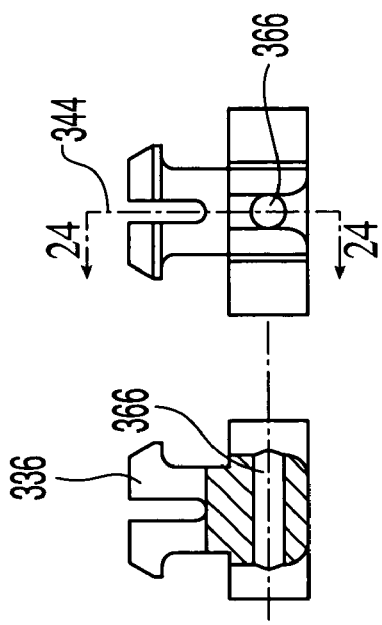
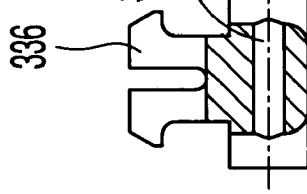

GRAFT FIXATION SYSTEM AND METHOD

FIELD OF THE INVENTION

The present invention relates to a ligament or tendon reconstruction fixation system and a method for reconstruction or replacement of a ligament or tendon wherein a soft tissue graft or a bone-tendon-bone graft is received within a bone tunnel.

BACKGROUND OF THE INVENTION

In arthroscopic surgery, a torn or ruptured ligament or tendon may be treated by attaching an end of a tendon or ligament graft to bone. The graft end may be secured to the bone by any of a variety of devices and techniques. One common procedure, for example, involves the replacement of the anterior cruciate ligament (ACL) of the knee. In such operations, a tunnel is typically prepared through the patient's tibia, across the interarticular joint and into the femur. A hamstring tendon graft or a bone-tendon-bone graft may be attached to an implantable graft fixation device or screw or the like which is frequently planted in the femoral tunnel to help anchor one end of the graft therein. The other end of the graft is secured in the bone tunnel in the tibia or otherwise secured to the tibia.

Known configurations of such implantable devices incorporate various methods of mounting the graft. Typically, the method of anchoring a graft to bone is dependent upon whether the graft is made of soft tissue, such as a hamstring tendon graft, or whether a bone-tendon-bone type graft is used. By way of example, one method for ACL reconstruction uses a bone-tendon-bone graft and an interference screw, which may be inserted into a bone tunnel parallel to the bone block of the bone-tendon-bone graft. According to this method, holes are typically drilled in the bone block for passing sutures, which serve to pull the graft through the tunnel and into place. The bone block is then anchored in the bone tunnel by inserting an interference screw in the tunnel adjacent the bone block. The compressive action of the screw threads against the bone block and tunnel walls is intended to anchor the bone block of the graft in place.

Alternatively, ACL reconstruction may be accomplished with a hamstring tendon graft. This type of graft has also been secured in a bone tunnel with an interference screw. In this situation, an interference screw may be wedged between the soft-tissue graft and the bone tunnel to anchor the end of the graft in the tunnel. Soft tissue graft fixation may alternatively be accomplished by placing a pin transversely through the femoral tunnel and through the loop of a hamstring graft which is doubled over the transverse pin. Fixation using the cross pin involves preparation of a bone tunnel for placement of the graft and an additional, transverse bone tunnel for the transversely oriented pin.

U.S. Pat. No. 5,931,840 to Goble et al. discloses a bone fixation device for a ligament anchor system. Goble discloses a two part assembly which includes a threaded footing having a longitudinal passageway which is anchored in a bone tunnel. A graft-holding component is then inserted and seated in the longitudinal passageway which extends through the footing. A threaded insertion tool is used to push and guide the graft holding component, with the graft trailing behind, into the bone tunnel. Thus, the graft material and the shaft of the insertion tool are adjacent to each other as the graft is guided into place. The two-part assembly is connected in the bone tunnel, and the insertion tool is then unscrewed and withdrawn from the tunnel.

Another ligament reconstruction graft anchor apparatus is disclosed in U.S. Pat. No. 5,152,790 to Rosenberg et al. The Rosenberg patent describes an anchor assembly having a rotatable cylindrical ring which is open at its ends and has suture tie slots or openings in the cylindrical ring for attaching a ligament graft thereto with sutures. An end of the rotatable ring is connected to a threaded sleeve having a longitudinal passageway which extends through the sleeve and has openings at both ends. After one or more grafts are sutured to the rotatable ring end of the anchor assembly, a driver instrument is inserted through the opening in the ring and into the opening in the threaded sleeve. The grafts are positioned around the shaft of the driver tool, and the tool is used to guide and drive the assembly into the bone tunnel. When the threaded sleeve is screwed into the bone tunnel, twisting of the cylindrical ring and grafts is minimized, because the ring is rotatable with respect to the threaded sleeve.

Known devices and methods for installing and anchoring soft tissue and bone-tendon-bone grafts suffer from inadequacies which can result in damage to the graft, excess trauma to the patient receiving the graft, and/or an increase in post-operative recovery time. In particular, many known devices and graft fixation methods do not allow for satisfactory tensioning of the graft. For example, when an interference screw is used to anchor one end of the graft in a bone tunnel, the screw typically must be removed in order to adjust graft tension. Such removal can cause the graft to tear. Many prior art fixation devices also cause the flexible graft material to twist upon installation or when tension is adjusted. Twisting of the graft is undesirable because it places unequal stresses on the graft, thereby lessening the probability of successful rehabilitation. Furthermore, some prior art anchor systems hold the graft in a manner which preloads the graft on one side and/or forces the graft to one side or the perimeter of the bone tunnel. When the graft is tensioned with a force which is not axially aligned, or when the graft is held along the perimeter of the bone tunnel, the graft may be subject to abrasion caused by motion of the graft against bone in the tunnel, and in particular at the tunnel exits. In addition, many prior art procedures for inserting and affixing grafts are complex and/or require multiple steps that increase the likelihood of trauma to the patient and may lengthen post-operative recovery and rehabilitation. Prior art methods of affixing implants to bone also tend to be severely constrained by the configurations of the implants, wherein generally only one specific procedure may be used to install an implant.

Thus, there is a need for a graft fixation system and method for reconstructing or replacing a ligament or tendon that overcomes the above-mentioned disadvantages and problems found in prior art devices and methods.

SUMMARY OF THE INVENTION

A graft fixation device, system and method are disclosed for reconstruction or replacement of a ligament or tendon preferably a soft tissue graft or bone-tendon-bone (BTB) graft received and implanted in a bone tunnel.

The fixation device secures one end of a graft to bone and comprises an implant body and a graft interface member having a graft holding portion and an implant coupling portion. The implant body has a recess at a first end which receives at least a portion of the implant coupling portion in a manner which permits the implant body to rotate independently of the graft interface member, and preferably connects the implant body to the graft interface member in a permanent manner. The graft holding portion has a central longitudinal axis and is configured and adapted to hold a graft in alignment with and preferably along the central longitudinal axis. The second end of the implant body may have an opening configured and adapted to receive an insertion tool to assist in implanting the fixation device.

The graft holding portion may take a variety of forms including an enclosed loop, such as an eyelet, a cage or a helical screw. The graft may be secured by wrapping the graft around the enclosed loop, surrounding it by a cage, crimping the cage, inserting the helical screw portion into the graft, or using staples, pins, nails, screws and other securing devices to attach the graft to the graft holding portion. The implant coupling portion may have a flexible post which may have a flared tip. One or more slots or cross-cuts may be provided in the flared tip and/or flexible post. The recess in the implant body may be provided with an undercut section which may facilitate attachment of the graft interface member to the implant body.

The cage embodiment of the graft interface portion may be configured and adapted for holding one of, or a portion of one of, the bone segments of the BTB graft. The cage or portions thereof may be crimped to secure the graft to the implant. In one embodiment, the cage has one or more longitudinal wall sections connected to a circular end wall segment. The longitudinal wall sections may include one or more openings which may be configured and adapted to receive staples, pins, nails, screws or the like for securing the bone to the cage. Alternatively, in addition to, or optionally, the longitudinal wall sections may be crimped.

In another embodiment, the cage may comprise two pieces which connect together to surround a portion of the graft. The two pieces of the cage may comprise a cage bottom portion and a cage top portion attachable to the cage bottom portion. The two or more pieces forming the cage may have one or more detents configured and adapted to attach the pieces together. The pieces of the cage also may have one or more fittings configured and adapted to receive the detent. The cage also may have one or more walls or wall portions. The wall(s) or wall portion(s) may have serrations or teeth on their interior surface to assist in holding the graft. The cage further may have openings to facilitate bone growth around the cage and to the graft.

The implant body has an outer surface at least a portion of which may contain threads for implantation into bone. The opening in the implant body for the insertion tool may have a portion which is hexagonally-shaped, keyed or shaped so that the insertion tool can rotate the body. Alternatively, in addition to, or optionally, the insertion tool opening may further have a portion which includes internal threads for mating with threads on the insertion tool to assist in connecting the insertion tool to the implant.

The present invention in one embodiment further comprises a graft fixation system for installing and securing a fixation device in a prepared bone tunnel. The graft fixation system comprises an implant body and a graft interface member coupled to the implant body preferably in a manner so that they are not easily separable and more preferably so that they are permanently attached, and which allows the graft interface to rotate independently of the implant body. The graft interface portion preferably is connected to the implant body so that a graft holding portion of the graft interface portion is aligned along the central longitudinal axis of the fixation device and so that the graft holding portion is adapted and configured to hold the graft aligned with and preferably along the central longitudinal axis. The implant body and graft interface portion may have the structure and features described above when describing the fixation device.

The fixation system further may include a driver comprising a shaft and an outer sleeve, the shaft may have a first end which is configured and adapted to engage the implant body and the outer sleeve also may have a first end which is configured and adapted to engage the implant body wherein the shaft is configured and adapted to slide within and relative to the outer sleeve by a predetermined distance. The first end of the driver shaft may be configured and adapted with threads to engage threads in a recess in the implant body. The first end of the driver outer sleeve may be configured and adapted to engage the recess in the implant body in a manner to rotate the implant body.

A method of attaching a graft to a bone in a surgical procedure where a tunnel is formed in a bone which is to receive the graft also is provided. The method comprises the steps of: (i) providing a fixation device having a body portion substantially permanently connected to a graft interface portion wherein the fixation device has a central longitudinal axis and the graft interface portion is rotatable with respect to the body portion about the central longitudinal axis; (ii) providing a graft having first and second opposing ends; (iii) attaching the first end of the graft to the graft interface portion along the central longitudinal axis; (iv) attaching the fixation device within the bone tunnel; (v) affixing the second end of the graft to bone while maintaining tension in the graft; and (vi) adjusting tension in the graft by turning the body portion in the bone tunnel without imparting substantial twist to the graft.

While a brief summary of the invention has been provided, it is to be noted, however, that this description is merely illustrative of the principals and concepts underlying the invention. It is contemplated that various modifications, as well as other embodiments will, without departing from the spirit and scope of the invention, be apparent to persons skilled in the art.

BRIEF DESCRIPTION OF THE DRAWINGS

Preferred features of the present invention are disclosed in the accompanying drawings, wherein similar reference characters denote similar elements throughout the several views, and wherein:

FIG. 8 is a perspective view showing the bottom portion of the cage of FIG. 7;

FIG. 11 is a cross-sectional view taken along the line 11—11 of the cage top portion of FIG. 9;

FIG. 12 is a side elevational view of the fixation device of FIG. 10, wherein the cage top is removed;

FIG. 21 is a perspective view of the swivel connector of FIG. 18;

FIG. 22 is a top elevational view of the swivel connector of FIG. 21;

FIG. 23 is a side elevational view of the swivel connector of FIG. 21;

FIG. 24 is a partial cross-sectional view taken along the line 24—24 of FIG. 23;

DETAILED DESCRIPTION OF THE PREFERRED EMBODIMENTS

Figure 1:
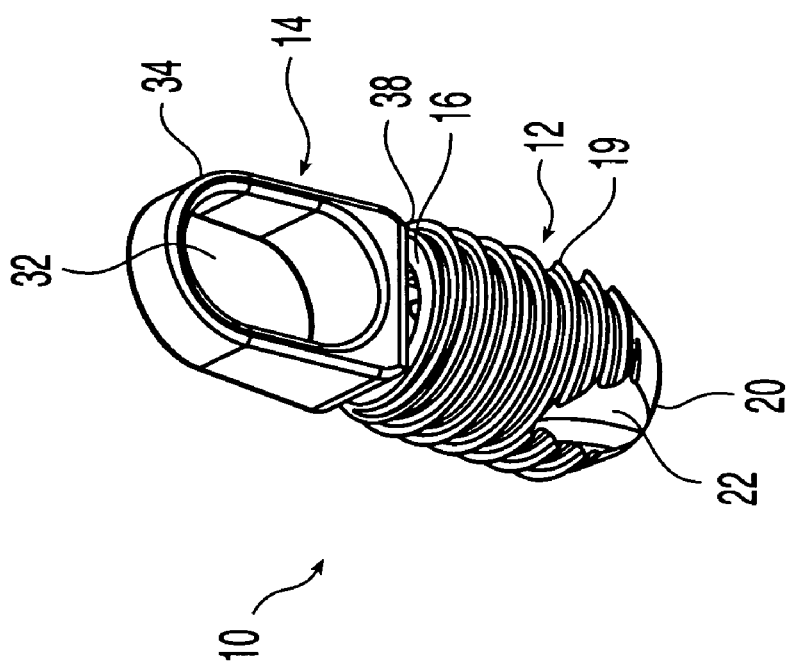
FIG. 1 is a perspective view of an embodiment of the graft fixation device for holding a soft tissue graft.

FIG. 1 illustrates a soft-tissue graft fixation device 10 according to an embodiment of the invention which may be used for implanting and affixing one end of a soft-tissue graft, such as, for example, a hamstring tendon graft, in a bone tunnel. Graft fixation device 10 includes body 12 and graft interface member 14 connected thereto.

Figure 2:
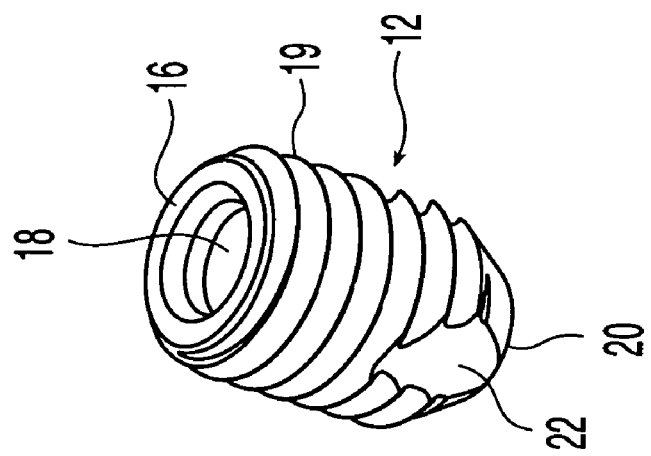
FIG. 2 is a perspective view of a body portion of the graft fixation device of FIG. 1.
Figure 4:
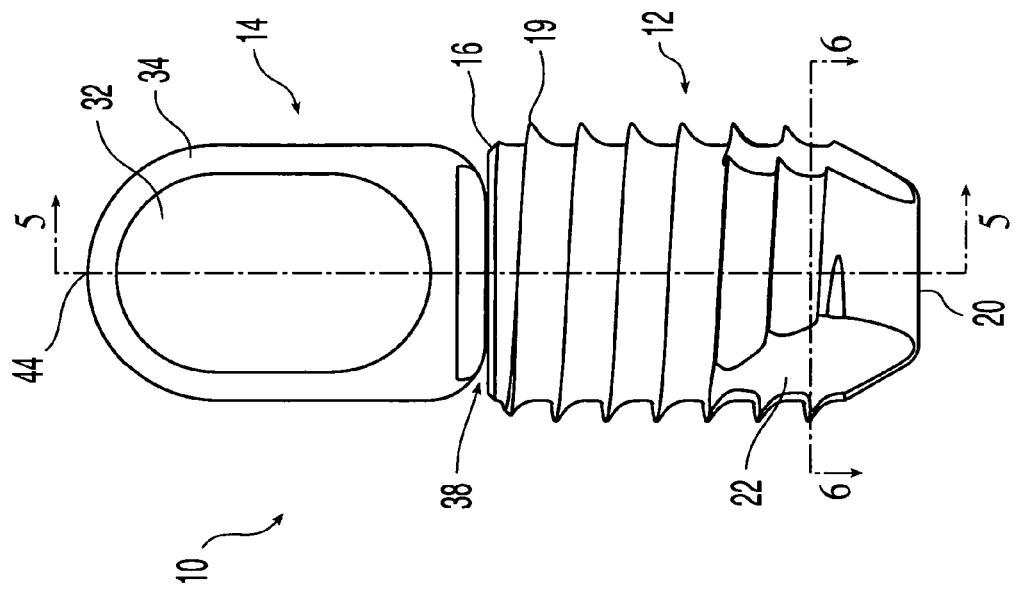
FIG. 4 is a side elevational view of the graft fixation device of FIG. 1.
Figure 3:
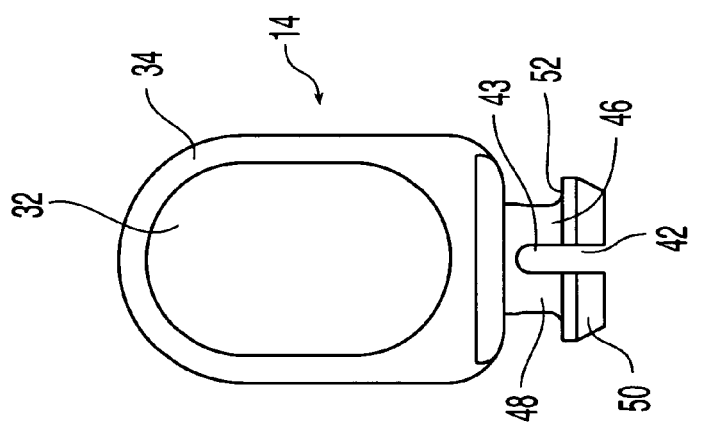
FIG. 3 is a side elevational view of the eyelet portion of the graft fixation device of FIG. 1.

Body 12 (FIG. 2) is the portion of the graft fixation device that may be anchored directly in a prepared bone tunnel. Body 12 may also be connected directly to graft interface member 14 (FIG. 3) which holds the graft. Body 12 and graft interface member 14 may be connected to form a two-piece assembly prior to implantation in a bone tunnel which preferably forms an integral construct which is not readily separable into its component parts, as illustrated according to a preferred embodiment in FIGS. 4 and 5. A coupling end 16 of threaded body 12 has a recess 18 for rotatably receiving graft interface member 14, as described below. Because body 12 may be secured directly to a bone tunnel, body 12 preferably is substantially inflexible and is preferably formed of bio-compatible metal. Graft interface member 14 is also preferably formed of a bio-compatible metal. Body 12 has an outer surface on which at least a portion contains self-tapping external threads 19 for insertion and implantation into a pre-drilled bone tunnel. Although threads on the outer surface of the body 12 are provided to implant the fixation device within the bone tunnel, it will be appreciated that other mechanisms for securing body 12 are well-known to those skilled in the art and also may be utilized.

Figure 6:
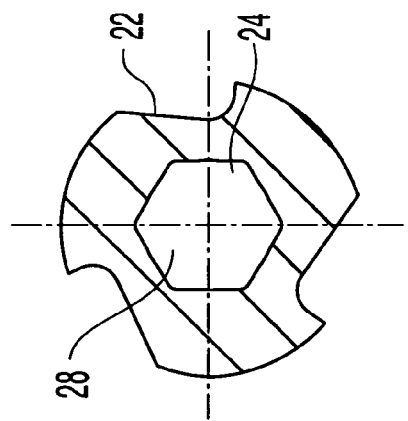
FIG. 6 is a cross-sectional view taken along line 6—6 of FIG. 4.
Figure 5:
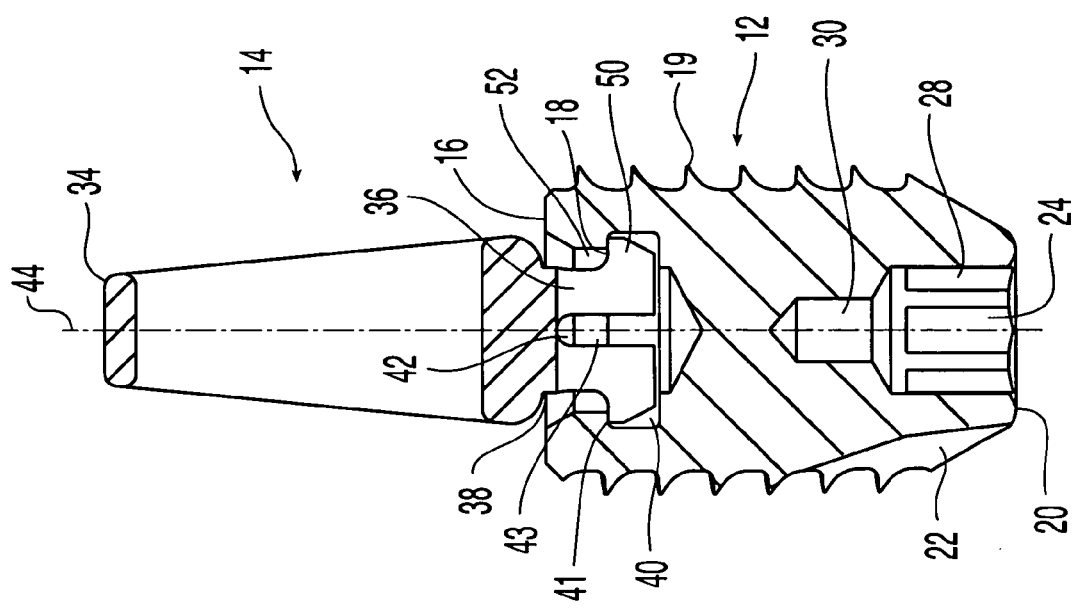
FIG. 5 is a cross-sectional view taken along the line 5—5 of FIG. 4.

Preferably, body 12 is reverse-threaded and may be driven into a bone tunnel using a threaded tool which may be attached to the proximal end 20 of the body 12, as explained in greater detail below. Of course, body 12 may alternatively have standard right-hand threads. The proximal end 20 of body 12 may have flutes 22 to facilitate tapping into a bone tunnel. Proximal end 20 preferably has an opening 24 for receiving a driver tool 26 (shown in FIG. 26), which may be used to pull or push fixation device 10 into a bone tunnel and to twist body 12 to drive its threads 19 into a bone tunnel wall. Preferably, opening 24 includes a hexagonal cavity 28 which tapers to an internally threaded portion 30, as illustrated in FIGS. 5 and 6. Both the hexagonal cavity 28 and internally threaded portion 30 may be dimensioned to mate with a retaining driver as described below.

According to one embodiment of fixation device 10, body 12 may be joined to graft interface member 14, referred to in the embodiment of FIGS. 1–6 as an eyelet portion, for implanting and attaching one end of a soft-tissue graft in a bone tunnel. Eyelet portion 14, illustrated in FIG. 3, may receive and hold a graft and may also connect with body 12. An enclosed loop 32 formed as part of eyelet portion 14 may receive an end of a soft tissue graft; the graft may be inserted through and wrapped around enclosed loop 32 and secured using, for example, sutures to keep the graft from separating from enclosed loop 32 (see, e.g., FIGS. 30–33). Preferably, enclosed loop 32 has softly radius-edge surfaces 34 to prevent injury to the graft. In addition, graft interface member 14 preferably has a flexible post 36 which forms part of a rotatable coupling 38 for connecting graft interface member 14 to body 12.

FIG. 5 illustrates rotatable coupling 38 having flexible post 36 inserted into recess 18 at coupling end 16 of body 12. Flexible post 36 is received in recess 18 so that it may rotate about longitudinal axis 44. As depicted in FIG. 5, recess 18 has an undercut section 40 for receiving flexible post 36 of graft interface member 14. Flexible post 36 preferably has at least one cross-cut 42 forming a slot 43 extending through the longitudinal axis 44 of the post portion to form post segments 46, 48. One skilled in the art can appreciate that multiple cross-cuts or slots may be formed in flexible post 36. Post segments 46, 48 may flex toward each other when squeezed together. Post 36 may also have a flared tip portion 50 that can be inserted into recess 18 of the threaded body 12. Upon insertion, post segments 46, 48 deflect elastically toward each other until the flared tip portion 50 reaches the undercut section 40, whereupon the flared tip portion 50 springs back to its undeflected position. The under-cut section 40 of the recess 18 forms a flange 41 which prevents the shoulder 52 of the flared tip portion 50 from passing back through recess 18. The body 12 and the graft interface member 14 are thus connected together, preferably permanently, yet they are free to rotate independently about longitudinal axis 44.

In another embodiment of the invention, illustrated in FIGS. 7–13, the fixation device 110 may be used to anchor one end of a bone-tendon-bone (BTB) type graft in a bone tunnel. For this embodiment, body 12 may be rotatably connected to an graft interface member 114 which is configured to hold a bone block or bone plug which forms one end of the BTB graft.

Figure 7:
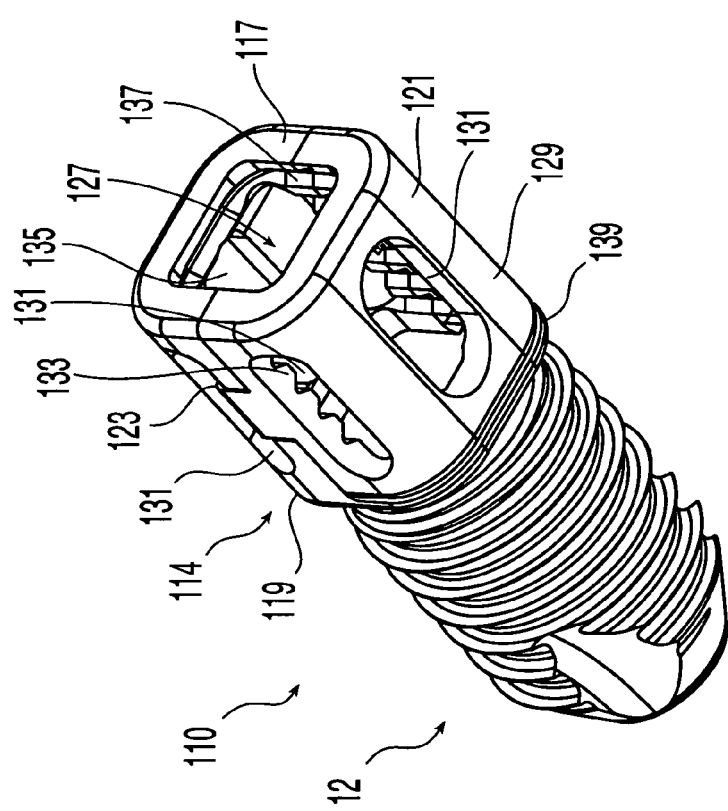
FIG. 7 is a perspective view of an embodiment of the graft fixation device having a cage for holding a bone block.
Figure 10:
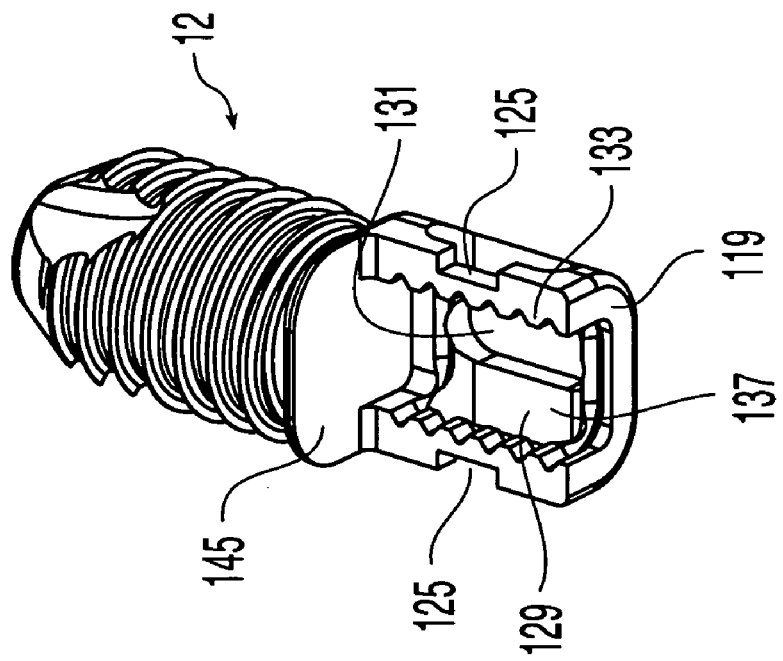
FIG. 10 is a perspective view of the embodiment of FIG. 7 with the cage top removed.
Figure 9:
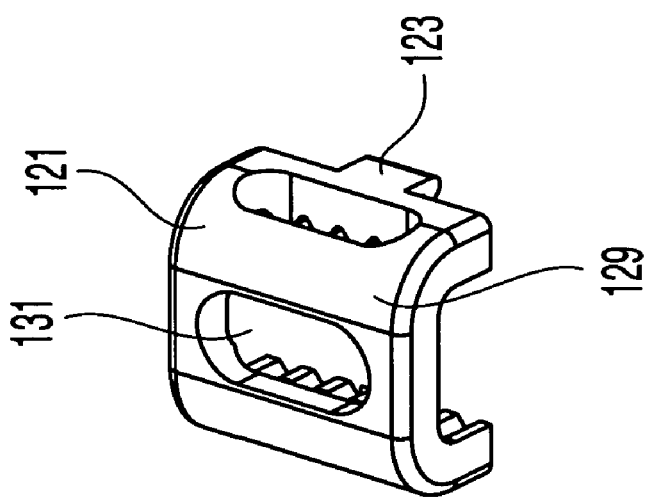
FIG. 9 is a perspective view of the top portion of the cage of FIG. 7.
Figure 14:
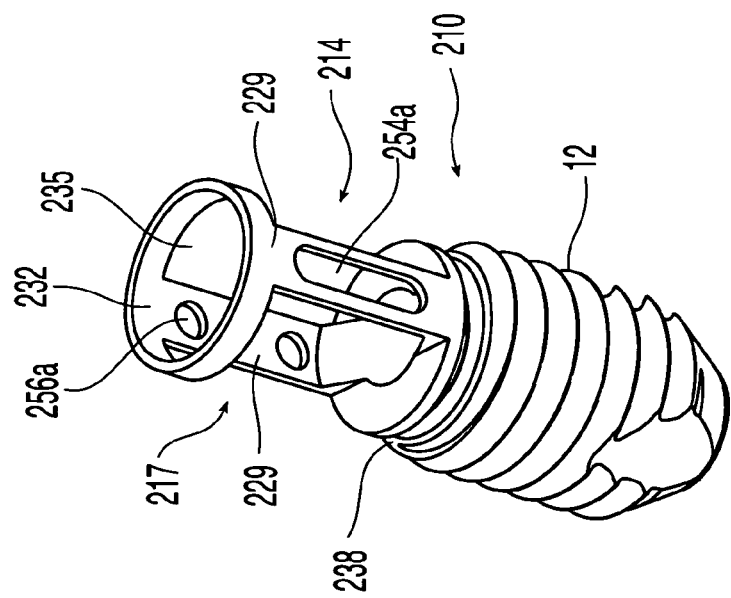
FIG. 14 is a perspective view of an embodiment of the graft fixation device having a one-piece bone block cage.
Figure 13:
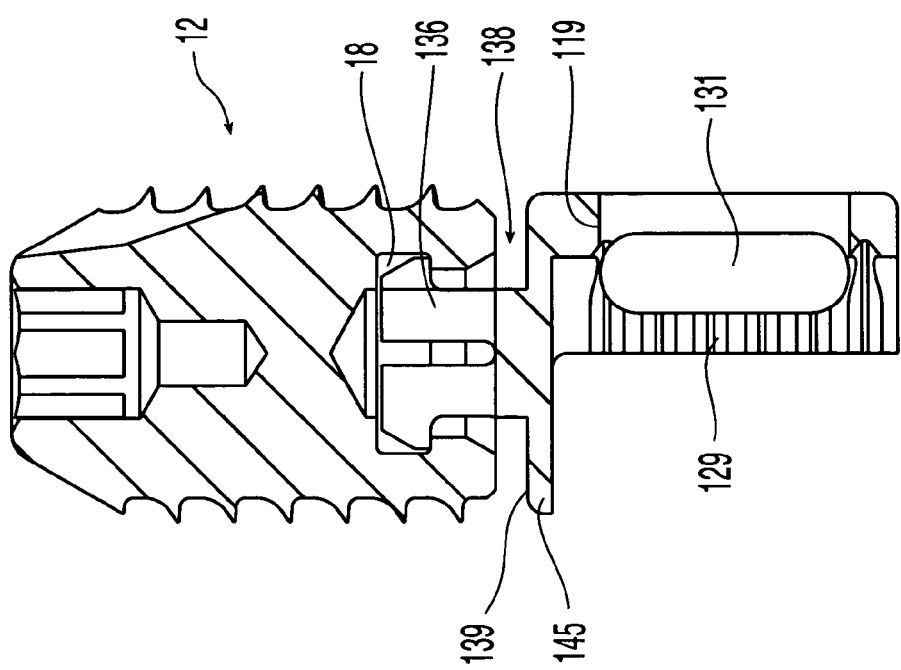
FIG. 13 is a cross-sectional view taken along the line 13—13 of FIG. 12, showing the engagement between the cage portion and the threaded body.

In the embodiment illustrated in FIG. 7, graft interface member 114 includes a bone block cage 117, in which the bone plug end of a BTB graft may be trapped and compressed. Cage 117 preferably includes cage bottom 119 and cage top 121, which are illustrated in FIGS. 8 and 9, respectively. One portion of the cage, preferably cage top 121, is removable from graft interface member 114 as illustrated in FIG. 10.

Preferably, cage bottom 119 and cage top 121 may be snapped together. As illustrated in FIGS. 9 and 11, cage top 121 may have detents 123 which enable cage top 121 to engage fittings 125 on cage bottom 119 so that the top and bottom portions of the cage 117 may be fastened together after a bone block has been positioned in an interior space 127 of cage bottom 119. Alternatively, after a bone block has been positioned in the interior space 127 of cage bottom 119, cage top 121 may be crimped over the bone to close the cage and secure the bone block therein.

The walls 129 of the cage may be provided with windows or openings 131 to encourage bony ingrowth and bone regeneration through the bone cage windows 131. Serrations or teeth 133 may be formed on an interior portion 137 of bone block cage 117 to provide a secure hold onto a bone block which is inserted therein. Cage 117 further includes an opening 135, illustrated in FIG. 7, to allow the remainder of the graft to extend away from the implant device. Flexible post 136 may extend longitudinally from wall 145 at the proximal end 139 of graft interface member 114 for connecting interface member 114 to body 12. Flexible post 136 mates with the recess 18 of the body, as described in the previous embodiment and illustrated in FIG. 13, to form rotatable coupling 138. The rotatable coupling 138 allows the interface portion 114 to rotate with respect to the implant body 12 about longitudinal axis 144.

Figure 16:
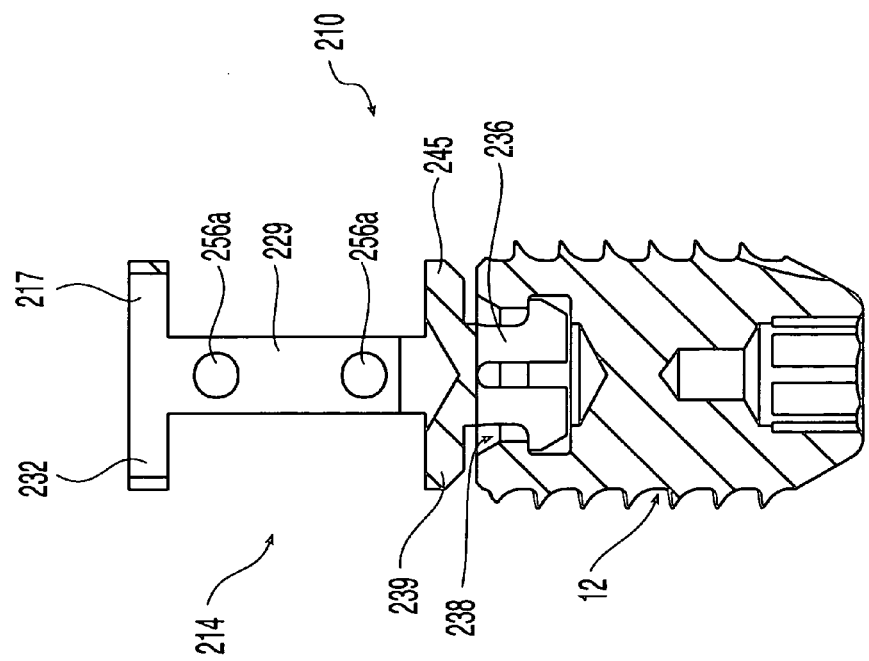
FIG. 16 is a cross-sectional view taken along the line 16—16 of FIG. 15, showing the engagement between the cage portion and the threaded body.
Figure 15:
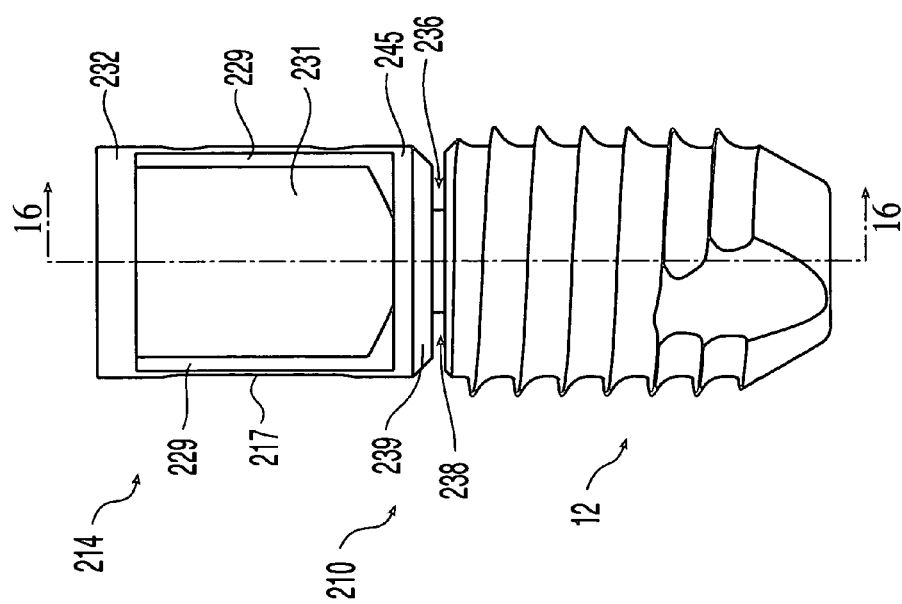
FIG. 15 is a side elevational view of the fixation device of FIG. 14.
Figure 17:
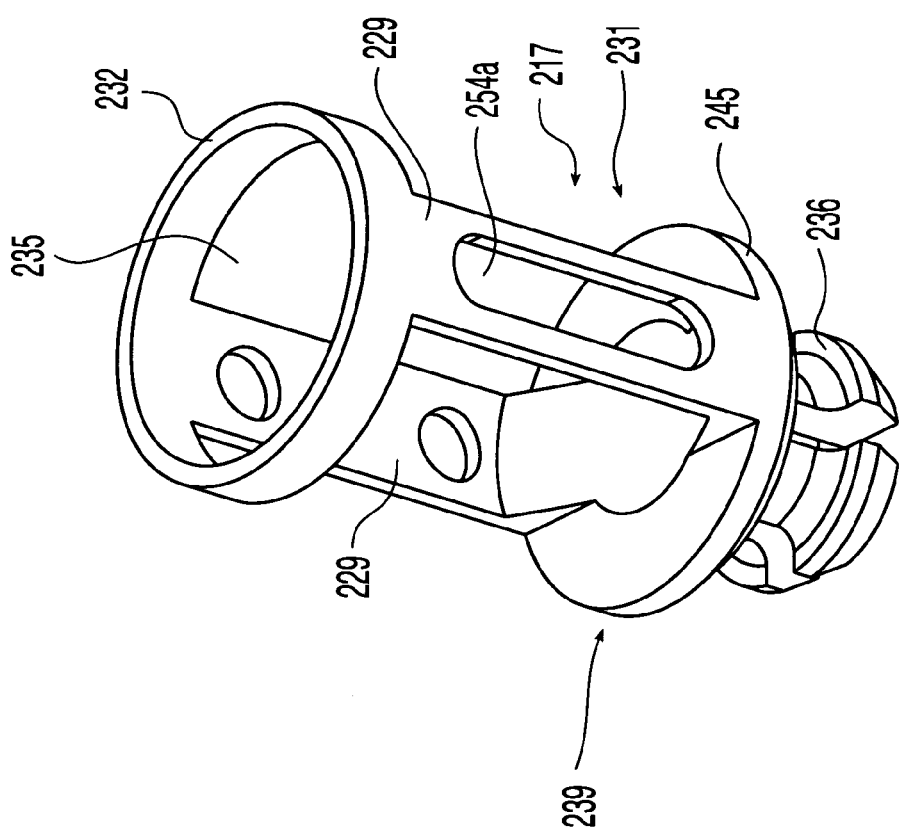
FIG. 17 is a perspective view of the one-piece bone block cage portion of FIG. 15.
Figure 20:
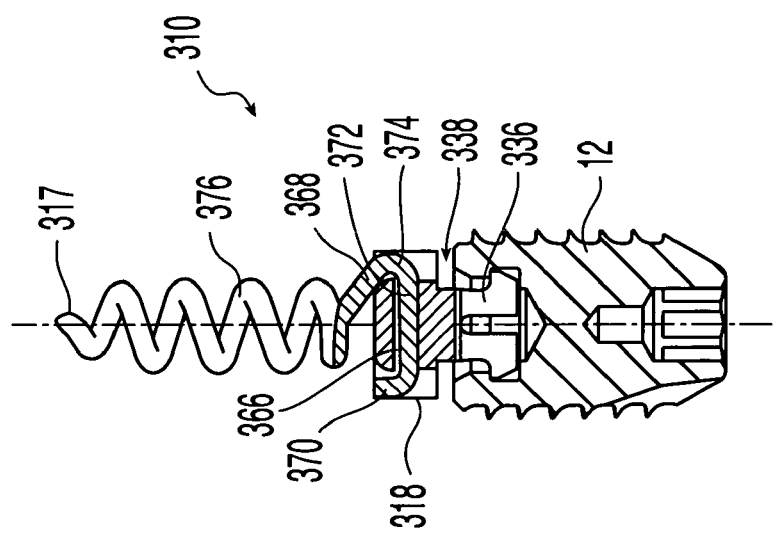
FIG. 20 is a cross-sectional view taken along the line 20—20 of FIG. 19.
Figure 19:
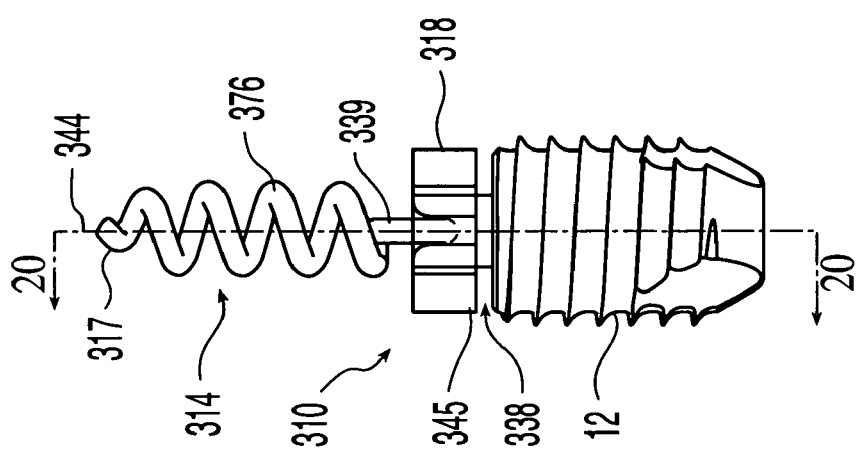
FIG. 19 is a side elevational view of the fixation device of FIG. 18.
Figure 18:
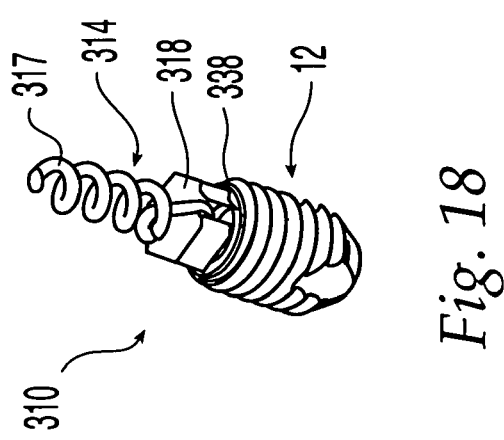
FIG. 18 is a perspective view of an embodiment of the graft fixation device.
Figure 25:
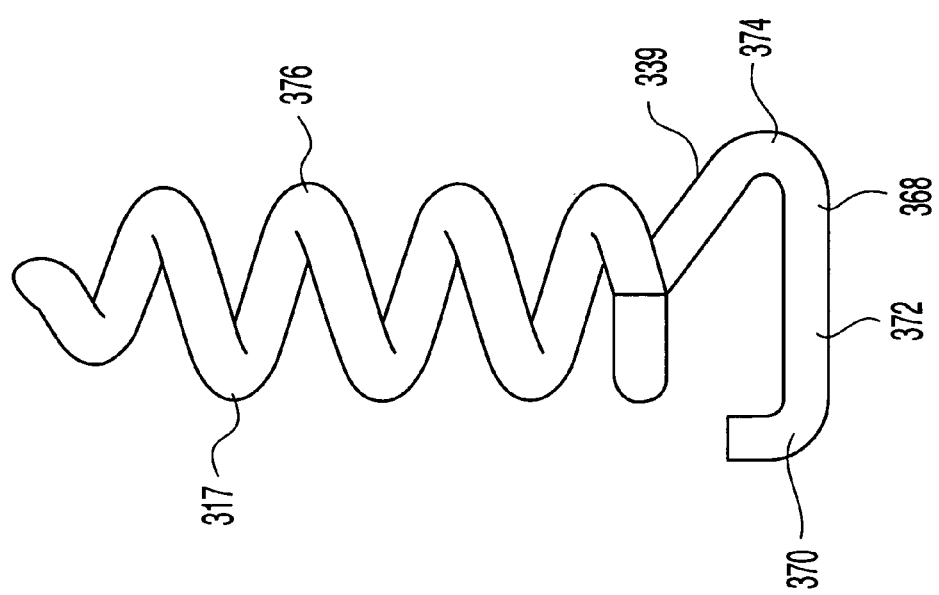
FIG. 25 is a side elevational view of the helical screw portion of the fixation device of FIG. 18.

According to yet another embodiment, the fixation device may provide a one-piece bone block cage for bone-tendon-bone graft reconstruction. As illustrated in FIGS. 14–17, fixation device 210 preferably includes a graft interface member 214 which has a one-piece cage 217 for holding a bone plug, and an implant body 12. Rotatable connection 238 is provided between graft interface portion 214 and body 12. According to the embodiment illustrated in FIG. 14, bone block cage 217 is a one-piece structure having longitudinal wall stem sections 229 and cut-out portions 231. Distal end 232 of bone block cage 217 has a circular opening 235 through which a bone plug or block may be inserted. As illustrated in FIGS. 16 and 17, proximal end 239 of cage 217 has a wall 245 having flexible post 236 extending longitudinally away from cage portion 217 for inserting into recess 18 in body 12 and attaching the bone block cage thereto. Wall sections 229 are preferably formed on opposite sides of cage 217 so that a bone block may be inserted therebetween.

After insertion of a bone block, wall sections 229 may be crimped inwardly to hold the bone block in place. Instead of or in addition to crimping a bone block in cage 217, wall sections 229 may be provided with one or more holes 254, 256 so that one or more staples (not shown) may be inserted through wall sections 229 and the bone block to hold the bone block in the cage. Cut-out portions 231 (FIG. 15) provide an openness to the cage 217 structure to encourage bone regeneration between a bone block in cage 217 and a bone tunnel in which the cage is inserted.

Another embodiment, graft fixation device 310, illustrated in FIGS. 18–25 may be useful for bone-tendon-bone reconstruction. Graft fixation device 310 preferably includes a graft interface member 314 which includes a helical screw member 317 for insertion into a bone plug and a swivel connector 318 for connection to body 12. Rotatable connection 338 is provided between a swivel connector 318 and threaded body 12. Swivel connector 318 includes a wall portion 345 having a flexible post 336 extending longitudinally away from wall portion 345 for inserting into recess 18 in body 12. Flexible post 336 may be configured and structured as flexible post 36 described above. Swivel connector 318 is independently rotatable with respect to body 12 about longitudinal axis 344.

Wall portion 345 may be hexagonally-shaped as shown having side surfaces 362 to fit a wrench or other instrument to rotate swivel connector 318. Slots 364 may be formed in side surfaces 362 with a passageway 366 extending through wall portions 345 between slots 364 as shown in FIGS. 23 and 24.

Helical screw member 317 has a proximal hook portion 368 at its proximal end 339 for connecting to swivel connector 318. Proximal hook portion 368 has a curved end section 370 connected to straight-extending section 372 followed by curved middle section 374 which transitions to helical screw section 376 which engages a bone portion of a BTB graft. Helical screw member 317 is connected to the swivel connector 318 so that extending section 372 traverses and resides in passageways 366 and curved sections 370, 374 reside in slots 364. In this manner, helical screw portion 317 is fixed to swivel connector 318 so that they do not rotate with respect to one another. In use, the helical portion is inserted into one of the bone blocks. A wrench or similar tool may grasp swivel connector 318 to assist inserting the helical screw member into the bone block. After the helical screw member is implanted into the bone block, the body 12 then may be threaded into the bone tunnel to attach to the bone. The body, swivel connector and helical screw member all are assembled as a unit during manufacture, preferably permanently, to form an integral construct.

The preferred embodiments of the fixation device attach the graft along a central longitudinal axis of the fixation device, thereby maintaining an equal distribution of force along the graft which facilitates alignment of the graft with the implant or fixation device. By holding the graft in centered alignment in a bone tunnel, the fixation device of the invention minimizes wear and abrasion to the graft, thereby ensuring more successful implantation and rehabilitation.

Figure 26:
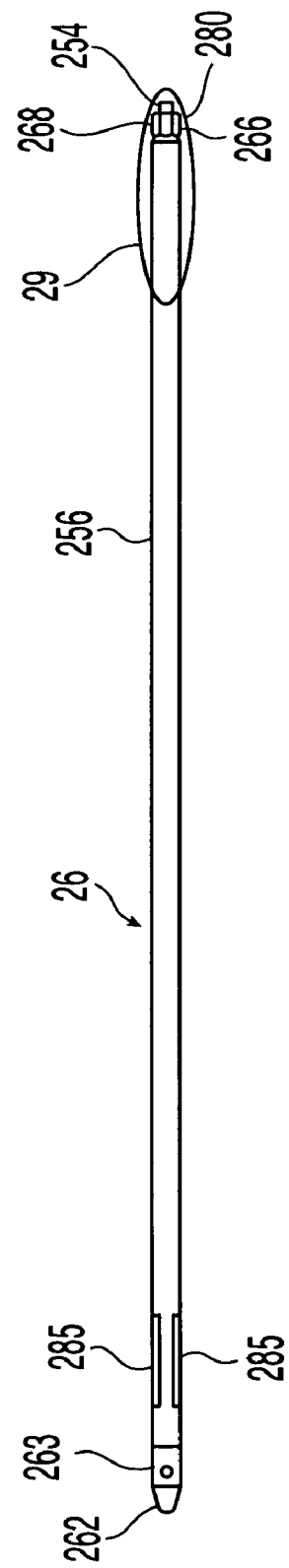
FIG. 26 is a side elevational view of an embodiment of a driver used in accordance with the method of the invention.
Figure 27:
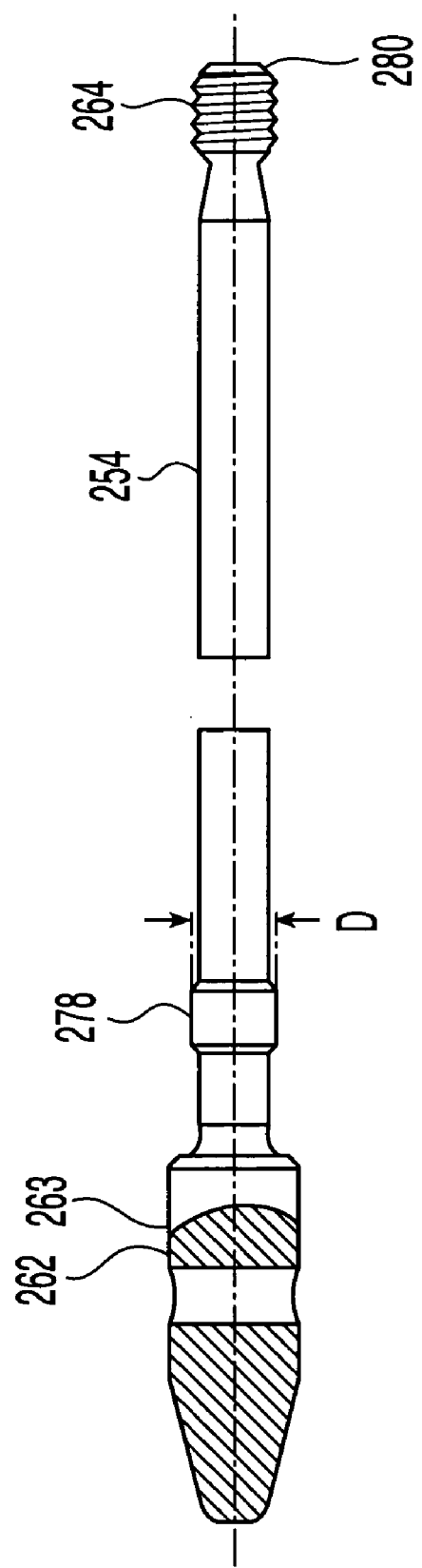
FIG. 27 is a side elevational view of a shaft portion of the driver of FIG. 26.
Figure 28:
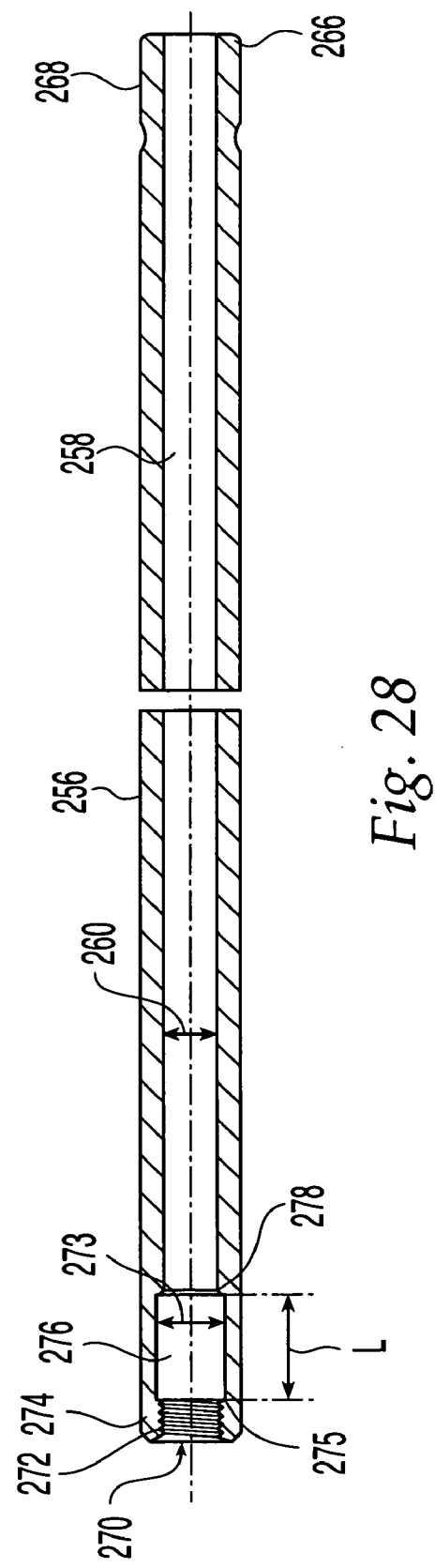
FIG. 28 is a side elevational view of an outer sleeve portion of the driver of FIG. 26.

A retaining driver 26 as illustrated in FIGS. 26–28 may assist in positioning and securing fixation device 10, 110, 210 or 310 and a graft into a suitably prepared bone tunnel. As described in greater detail below, retaining driver 26 may be used to push or pull fixation device 10, 110, 210 or 310 into a bone tunnel and drive or screw body 12 into the tunnel. Thus, driver 26 preferably is releasably attachable to the proximal end 20 of body 12. The preferred way of attaching driver 26 to body 12 enables the driver and the fixation device to stay together when subjected to tension, e.g., when the driver is used to pull the fixation device into a bone tunnel, and when torqued, e.g., when the driver is turned to cause threads 19 to cut into and engage the wall of the bone tunnel.

Figure 29:
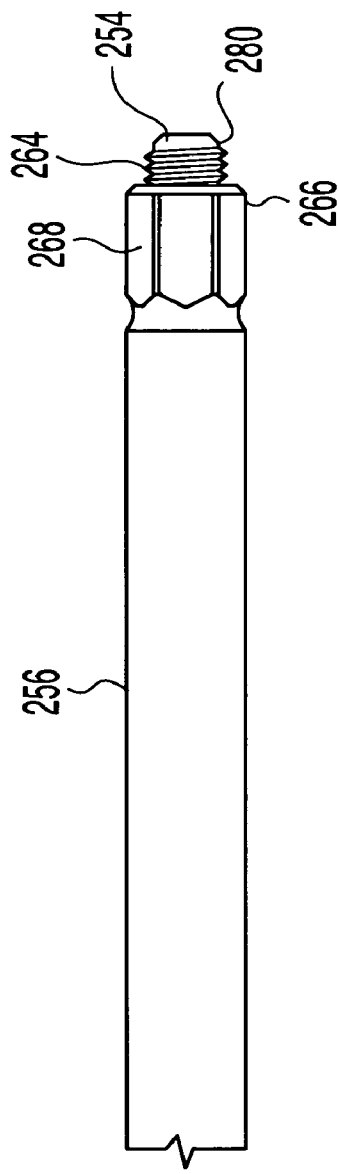
FIG. 29 is a side elevational detail of the distal end of the driver of FIG. 26, showing one end of the driver shaft protruding from one end of the outer sleeve.

According to a preferred embodiment illustrated in FIG. 26, driver 26 includes shaft 254 surrounded by an outer sleeve 256. Shaft 254 (see FIG. 27) has a proximal end 262 which includes a handle portion 263, which is preferably textured to enable the operator to grip, hold and/or twist shaft 254 easily. Distal end 280 of shaft 254 preferably has external threads 264 (not shown) which may mate with body 12 at internal threads 30 (see FIG. 5). Distal end 280 of the shaft, including external threads 264, may be guided into outer sleeve 256 at proximal end 274. FIG. 28 illustrates outer sleeve 256 with a hollow interior 258 having a first interior diameter 260. First diameter 260 is sufficient to permit axial movement of shaft 254 inside sleeve 256. Distal end 266 of outer sleeve 256 preferably has external hexagonal coupling portion 268, illustrated in FIG. 29, which may be inserted into hexagonal cavity 28 of body 12 (see FIGS. 5 and 6).

Shaft 254 and sleeve 256 may slide longitudinally relative to each other along a predetermined portion of the longitudinal axis of retaining driver 26. Accordingly, portions of shaft 254 and sleeve 256 may be configured to allow a predetermined amount of relative axial motion. Preferably, for example, sleeve 256 has an opening 270 having internal threads 272 at proximal end 274, as illustrated in FIG. 28. Internal threads 272 terminate at a cavity 276 inside sleeve 256, wherein cavity 276 has a diameter 273 which is greater than first interior diameter 260 of hollow interior 258. Cavity 276 may extend along a predetermined length L of the interior portion of sleeve 256 from proximal end 275 to distal end 277, as illustrated in FIG. 28. Also, according to a preferred embodiment illustrated in FIG. 27, shaft 254 may have external threads 278 near proximal end 262 of the shaft. External threads 278 have a maximum diameter D that is wider than the remainder of shaft 254 that is distal to threads 278. Also, threads 278 are engageable with internal threads 272 at opening 270 of sleeve 256. Thus, the distal end 280 of shaft 254 may be inserted into the proximal opening 270 of sleeve 256 and pushed therethrough until external threads 278 of the shaft engage internal threads 272 of the sleeve Shaft 254 may then be screwed into sleeve 256 until external threads 278 extend into cavity 276, enabling shaft 254 to slide axially with respect to sleeve 256 through a distance which is limited by length L of cavity 276. Therefore, threads 278 may permit limited axial travel of shaft 254 inside sleeve 256 due to the predetermined length L of cavity 276 in which threads 278 may slide.

Threads 278 also may serve to prevent shaft 254 from accidentally sliding out of sleeve 256. Keeping the components 254 and 256 of the driver 26 together helps to preserve sterility of the driver and to simplify its handling, particularly during a surgical procedure. Although it is preferable to provide internal threads 272 in sleeve 256 to prevent the shaft from accidentally sliding out of the sleeve, it is contemplated that other structures, known to those having ordinary skill in the art, may be provided for such purpose or that threads 272 may be omitted. Furthermore, although it is preferable to provide driver 26 with external threads 278 and cavity 276, it will be readily apparent to those of ordinary skill that other geometries may be employed to permit limited travel between shaft 254 and sleeve 256.

Thus, shaft 254 may be slid axially so that distal end 280 withdraws inside sleeve 256 or protrudes outside sleeve 256 beyond its distal end 266. In the detail view of FIG. 29, distal end 280 of shaft 254 protrudes outside the distal end 266 of sleeve 256. When distal end 280 protrudes outside sleeve 256, external threads 264 may be screwed into threaded portion 30 of recess 18 in body 12 (shown in FIG. 5). While shaft 254 is thus engaged with body 12, hexagonal coupling portion 268 of outer sleeve 256 may also be engaged with hexagonal cavity 28 of body 12. Alternatively, outer sleeve 256 may be disengaged from threaded body 12 so that only the shaft portion 254 of driver 26 remains engaged with body 12. When threaded end 264 is withdrawn fully inside sleeve 256, driver 26 may be releasably connected to body 12 by inserting hexagonal coupling portion 268 into hexagonal cavity 28. Because shaft 254 and sleeve 256 may slide relative to each other, either shaft end 264 or sleeve end 266, or both, may engage proximal end 20 of body 12.

Driver 26 preferably also has flat portions 285 on outer sleeve 256 for engaging a standard tool such as a T-handle for turning the outer sleeve of the driver. When a ratcheting T-handle is releasably attached to outer sleeve 256 at flat portions 285, outer sleeve may be turned while shaft 254 may remain stationary. Thus, when outer sleeve 256 is connected to body 12, and a T-handle engages the outer sleeve at flats 285, outer sleeve may be twisted so as to turn the body about its longitudinal axis 44.

Driver 26 is therefore capable of exerting a pulling or pushing force on the fixation device of the invention and independently exerts torque on the fixation device. Attachment of driver 26 to the fixation device thus enables the device 10, 110, 210 or 310 to be pulled or pushed into a bone tunnel and then turned so that threads 19 of body 12 may tap into the bone and anchor the device thereto. It is to be understood, however, that the specific configuration described herein for coupling driver 26 to body 12 is only one of a number of configurations which could be used to achieve a releasable connection therebetween. For example, the cross-sectional geometry of cavity 28 on body 12 and of coupling portion 268 on driver 26 need not be hexagonal. Instead, any geometry known to those of ordinary skill in the art may be used as long as it provides a releasable coupling enabling driver 26 to apply torque to body 12. Preferably, the ability of driver 26 to transfer torque is independent of its ability to pull or push body 12 longitudinally. It should also be understood that the coupling between driver shaft 254 and threaded body 12 is not limited to a coupling between external threads 264 on shaft 254 and internally threaded portion 30 on threaded body 12. Those of ordinary skill in the art will recognize that any one of a variety of known configurations may be used for a releasable coupling which allows driver 26 to push or pull threaded body 12 in an axial direction.

The preferred embodiments of the inventive fixation device may be implanted or affixed to a bone tunnel according to a one-step graft insertion/fixation method wherein the graft is preferably connected to the fixation device before implantation in a bone tunnel. As used herein, the term "one-step" refers to the preferred method, in which the implant and the graft may be inserted into the tunnel while they are attached to each other, rather than in two separate steps.

Preliminarily, a soft-tissue graft or a bone-tendon-bone graft is obtained or harvested and is secured to an appropriate graft interface portion, such as, for example, one of the embodiments described above. A soft-tissue graft, for example, may be attached to an embodiment of the fixation device which has an eyelet loop portion, such as the embodiment illustrated in FIGS. 1–6. An end of a bone-tendon-bone graft, on the other hand, is preferably attached to an embodiment capable of securely holding a bone block or bone plug, such as, for example, one of the embodiments illustrated in FIGS. 7–13, 14–17 or 18–25. Preferably, the graft interface member 14, 114, 214 or 314 is connected to body 12 by a permanent, rotatable connection such as, for example, rotatable coupling 38, 138, 238, 338 between the interface member and the implant body. Such a connection ensures that the implant/graft fixation device is securely and permanently held together, yet the implant body portion 12 is free to rotate about the longitudinal axis 44 of the device independently of a graft attached to the interface member 14, 114, 214 or 314.

The fixation device may be inserted and affixed in a bone tunnel according to a method wherein graft interface member 14, 114, 214 or 314 is preferably connected to body 12 prior to attachment of the graft to the interface member. Any one of the embodiments of the fixation device described hereinabove may be selected for use with the method, depending on the type of graft which is chosen. For example, a soft tissue graft is preferably attached to fixation device 10 at enclosed loop 32. Preferably, the soft tissue graft is sutured to itself and/or eyelet loop 32 to ensure that the graft will not fall off fixation device 10. A bone-tendon-bone graft may be attached to a fixation device 110, 210 or 310 which secures the bone block at one end of the graft to the fixation device or implant.

When using fixation device 110, as exemplified by FIGS. 7–13, a bone block at one end of the graft may be placed into cage bottom 119 (shown in FIG. 8) and cage top 121 may then be attached to the cage bottom by, for example, inserting and snapping detents 123 into fittings 125. Serrations 133 bite into the bone block, while windows 131 provide openings to promote bony ingrowth and regeneration between the bone block and a bone tunnel into which the fixation device is to be inserted. Alternatively, a graft having a bone block at one end may be attached to fixation device 210, which provides a one-piece bone block cage 217 such as that illustrated in FIGS. 14–17. To use the one-piece bone block cage embodiment, the bone block at one end of the graft is inserted axially into opening 235 at distal end 232 of cage 217. The bone block may be secured to cage 217 by one of several methods such as, for example, crimping longitudinal wall sections 229 against the bone block or by inserting one or more staples through holes 254 and/or 256 into the bone block.

Once the fixation device and graft are secured to each other, they are ready to be implanted in a bone tunnel. Although the device and method may be used in a variety of ligament repair or replacement procedures, the description which follows exemplifies the method by describing how it may be applied to an anterior cruciate ligament (ACL) reconstruction procedure.

Preliminarily, an appropriate bone tunnel is prepared according to known methods. These bone tunnels are drilled in and through the tibia and femur before inserting and affixing a fixation device or graft. The tibial tunnel extends from the tibial cortex below the knee joint to the intra-articular space of the knee joint. The femoral tunnel extends from the intra-articular space to the superolateral surface of the femur. Thus the prepared tunnels meet in the intra-articular space of the knee joint at the attachment sites of a torn or ruptured ACL.

Figure 30:
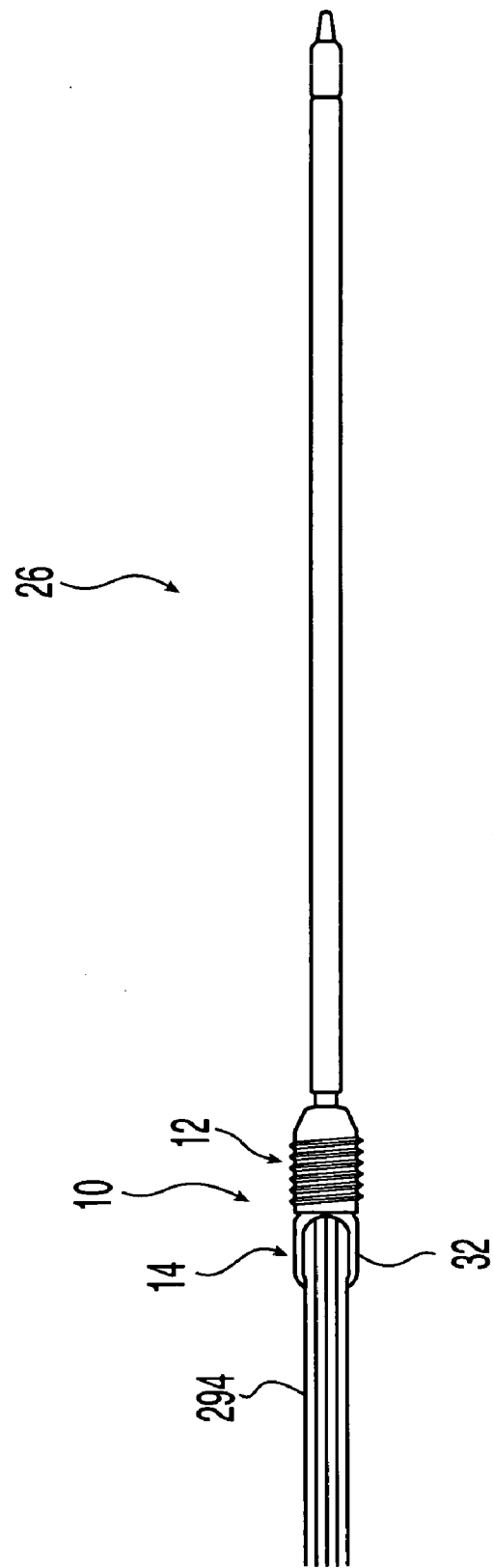
FIG. 30 is a side elevational view of the fixation device connected to a driver and a graft.
Figure 31:
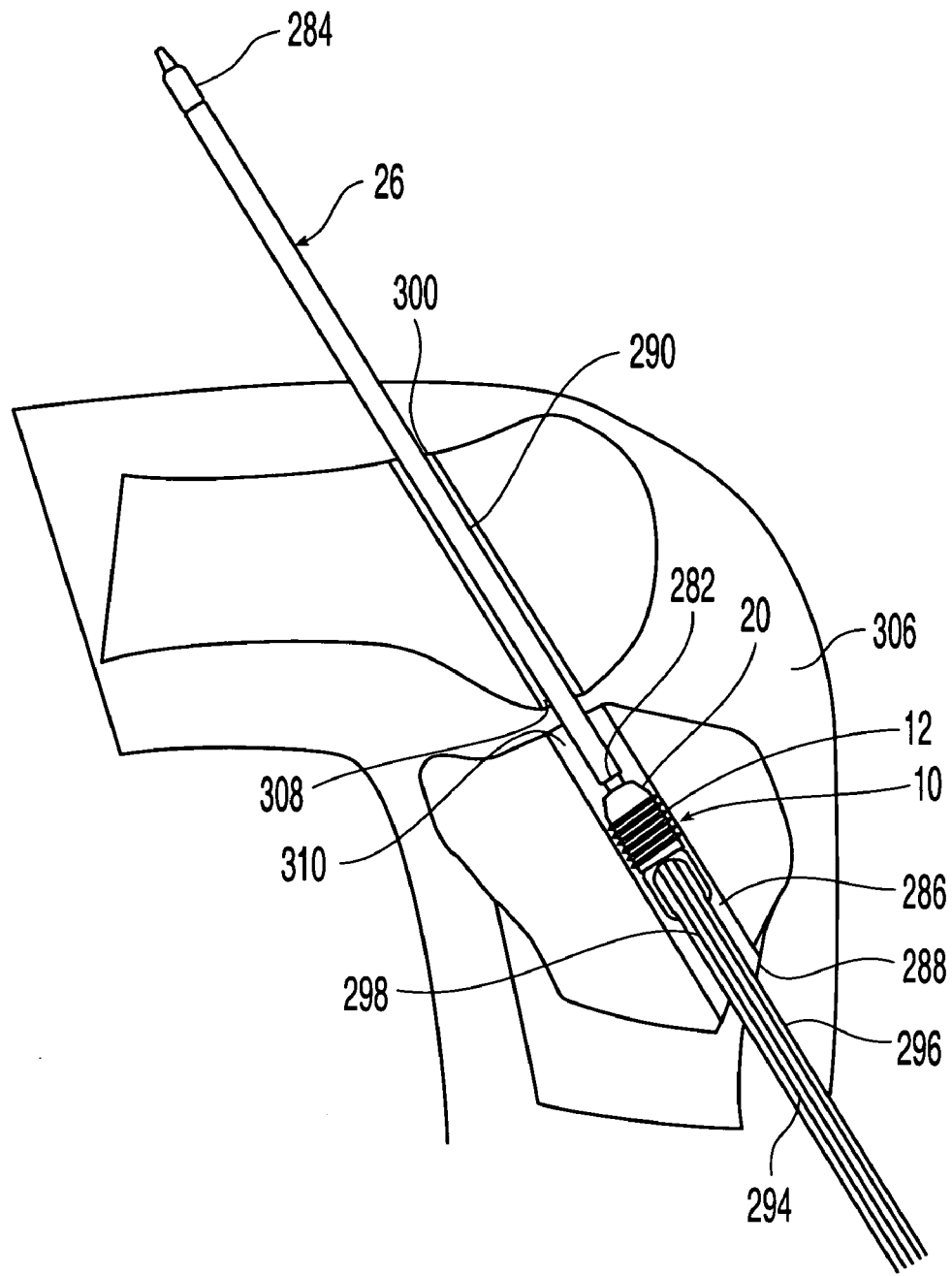
FIG. 31 is a side elevational view of a patient's knee illustrating an anterior cruciate ligament tunnel formed therein, wherein a soft-tissue graft attached to the fixation device is being pulled into the tunnel with a driver.
Figure 32:
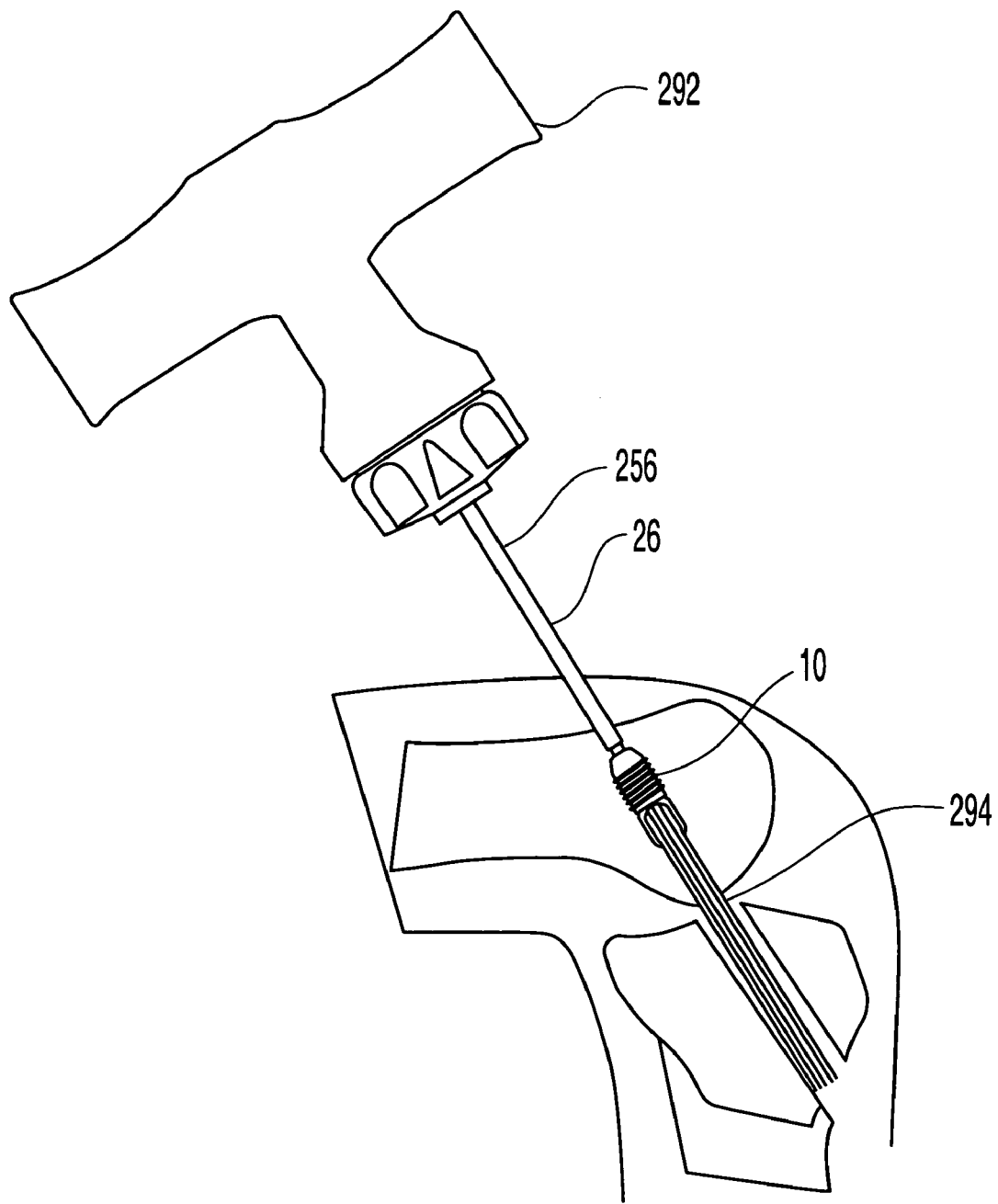
FIG. 32 is a side elevational view of a patient's knee illustrating an anterior cruciate ligament tunnel formed therein with a soft graft attached to a graft fixation device being pulled into the tunnel by a T-handle attached to a driver.

According to a preferred method of the invention, one fixation device 10, 110, 210 or 310 is attached to one end of a graft while the opposite end of the graft remains free as illustrated in FIG. 30. FIG. 31 illustrates one example of a method of inserting a soft tissue graft and fixation device 10 into prepared bone tunnels 286 and 290. As illustrated in FIG. 31, a driver tool, preferably retaining driver 26, may be attached at its distal end 282 to fixation device 10, 110, 210 or 310 at proximal end 20 of body 12. Preferably, body 12 has been previously attached to the graft interface portion 14, 114, 214 or 314, and a graft has been secured to the interface portion. Preferably, both shaft 254 and outer sleeve 256 of the driver are connected to implant body 12. The proximal end 284 of driver 26 is then inserted into the prepared, enlarged tibial femoral tunnel 286 at tibial cortex tunnel entrance 288. Tibial tunnel 286 preferably is enlarged so that fixation device 10, 110, 210 or 310 can be passed through without the threads engaging the side walls of the tunnel. Driver 26 is guided into and through the prepared tibial tunnel 286 and through femoral tunnel 290 until proximal end 284 protrudes from the superolateral tunnel entrance 300 as shown in FIG. 31. Driver end 284 is then pulled out of femoral tunnel 290 so that the fixation device and graft 294 may be pulled and guided through the prepared enlarged bone tunnel 286. According to this method, graft 294 trails behind the fixation device 10, 110, 210 or 310. Driver 26 is thus used to pull the fixation device until the proximal end 20 of body 12 engages femoral tunnel 290. Preferably some tension is applied to the graft 294 as it is guided into and through the bone tunnel or tunnels to minimize abrasion to the graft. When body 12 reaches the desired position, a tool such as a ratcheting T-handle 292 (FIG. 33) may be connected and used to advance the body 12 and cause threads 19 to tap into the femoral bone tunnel.

As described previously, a T-handle or similar instrument may be mounted on outer sleeve 256 of driver 26, preferably at flat portions 285, wherein flat portions 285 may engage the teeth of a T-handle, thereby enabling the T-handle device to grab onto sleeve 256 and apply a torque thereto. Also as described previously, threads 19 on threaded body 12 may be reverse-threaded. Thus, a T-handle with a standard right-hand throw may be used to drive sleeve 256 and turn it to cause body 12 to turn in the bone tunnel. In such a manner, the self-tapping threads 19 of body 12 engage bone in the bone tunnel. Adjusting the position of the fixation device may also be accomplished by turning outer sleeve 256 of driver 26 to drive body 12 to the desired location in bone tunnel 290. The end 298 of the graft 294 which is attached to the fixation device may be secured in femoral tunnel 290 as described. Alternatively, it may instead be preferable to pull the fixation device and graft through the femoral tunnel 290 to the tibial tunnel 286 so that the fixation device is anchored in tibial tunnel 286.

Alternatively, instead of attaching fixation device 10, 110, 210, 310 to the distal end 282 of driver 26 before passing proximal end 284 into the prepared bone tunnel, driver 26 may first be guided through a bone tunnel and then connected to the proximal end 20 of body 12. For example, for an ACL reconstruction procedure, a graft 294 may be prepared and attached at its end 298 to an implant 10, 110, 210 or 310. A driver tool such as driver 26 may then be inserted into the superolateral entrance 300 of femoral tunnel 290 and guided until distal end 282 protrudes from the tibial cortex entrance 288 of the tunnel. The distal end of the driver 26 may then be secured to the fixation device 10, 110, 210, 310 by, for example, screwing together threads 264 on the driver shaft to internally threaded portion 30 of body 12. Coupling portion 268 of outer sleeve 256 may also be connected to body 12 at opening 24. The driver may then be used to pull the implant 10, 110, 210 and graft into the bone tunnel. The fixation device 10, 110, 210, 310 may be screwed into the femoral tunnel in the desired location. Instead of pulling the fixation device up through the tibial tunnel and into the femoral tunnel, it will be apparent to those of ordinary skill in the art that the fixation device may alternatively be pulled from the femoral tunnel entrance 300 and guided through the bone tunnels so that it may be turned and anchored into tibial tunnel 286.

Alternatively, according to another method, a device such as a suture passer may be used to assist in pulling the free end of the graft into and through the bone tunnel. Preferably, some tension is applied to the graft 294 as it is guided into and through the bone tunnel or tunnels to minimize abrasion to the graft. If the graft is being pulled up from the tibial cortex entrance 288, the fixation device attached at the trailing end of the graft eventually approaches the tunnel entrance 288, and graft interface member portion 14, 114, 214 or 314 is guided into the bone tunnel 286. Driver 26 is connected to the trailing end 20 of the fixation device at opening 24 in implant body 12. Preferably, a handle such as a ratcheting T-handle 292 (FIG. 32) is secured to flat portions 285 of driver 26 so that the operator may turn the driver and cause the threads 19 of implant body 12 to tap into the bone tunnel. Because the fixation device has a rotatable coupling 38, 138, 238 or 338, turning body 12 does not impart, substantial twist to the graft which is attached to the fixation device.

The free end 296 of graft 294 may be secured to the bone tunnel by any one of a variety of methods known in the art, such as, for example, by inserting an interference screw through an arthroscopic portal 304 (not shown) to wedge proximal end 296 of graft 294 into bone tunnel 286. Alternatively, depending upon how and where the fixation device and graft are installed, the proximal end of the graft may be secured to the bone with staples. Alternatively, the approach may be reversed with the fixation device 10, 110, 210 or 310 inserted into the femoral tunnel 290 and secured in the tibial tunnel 286. According to this alternative method, fixation device 10, 110, 210 or 310 is guided and threaded into tibial tunnel 286 and the free end 296 of graft 294 may, for example, be stapled near the superolateral entrance 300 of femoral tunnel 290 according to methods of stapling which are known.

Alternatively, a second fixation device such as device 10', 110', 210' or 310' may be secured to graft end 296, so that each end of the graft is attached to a fixation device before implantation into a bone tunnel or tunnels. As used herein, a superscript "'" placed after a reference number indicates that a second device is being used. To implant a graft which is attached to fixation devices at both ends 296, 298 of the graft, for example, it may be preferable to use two driver tools 26 and 26', wherein each driver is attached to an implant body at opposite ends of the graft. For an ACL reconstruction procedure, driver 26 may first be connected to proximal end 296 of the graft. At the same time, a second driver 26' is attached to a second fixation device 10', 110', 210' or 310' at the distal end 298 of the graft. The driver 26 may be inserted into tunnel opening 288 or 300 and guided through both tibial and femoral tunnels until driver 26 protrudes from the opposite tunnel opening 300 or 288, respectively. At this point, driver 26 is used to pull and guide fixation device 10, 110, 210 or 310 and the proximal end 296 of the graft through the bone tunnel. Both drivers 26 and 26' may be used to guide the fixation devices and the graft therebetween into and through the bone tunnels 286 and 290. Drivers 26 and 26' may also be turned independently of each other to turn bodies 12 and 12' and cause their threads to tap into the respective bone tunnels 286 and 290.

When fixation devices are attached to both ends 296 and 298 of a graft, the graft may alternatively be implanted using an arthroscopic portal that is formed in the knee joint 306 during the surgical procedure. Accordingly, driver shaft 254 may be attached to body 12 of a fixation device 10, 110, 210 or 310 at one end 296 of the graft, and shaft 254 may be guided through a prepared bone tunnel such as femoral tunnel 290 from its entrance 308 at the interarticular joint 306 to superolateral entrance/exit 300. Driver 26 may then be used to anchor the fixation device (10, 110 or 210) in the femoral tunnel. A similar procedure may then be followed to install a second fixation device (10', 110' or 210') which is attached to the opposite end 298 of the graft into the tibial tunnel 286, by guiding the second fixation device and graft end 298 into the tibial tunnel via entrance 310 at the interarticular joint 306.

Once both ends of the graft have been secured, any desired adjustments in tensioning may be accomplished by turning sleeve 256 with the aid of a handle such as T-handle 292. Distal end 266 of sleeve 256 engages the proximal end 20 of body 12 so that the driver 26 may apply torque to the threaded body, thus enabling adjustment of the position of the threaded body in the bone tunnel. Because the fixation device 10, 110, 210, 310 has a rotatable coupling 38 between body 12 and the graft interface member 14, 114, 214 and 314, the body may be turned in the bone tunnel without imparting significant twist to the graft interface member or the graft attached thereto. Thus, tensioning of the graft may be accomplished without undesirable twisting by adjusting the position of body 12.

Additionally, the configuration of fixation device 10, 110, 210 or 310 enables the graft to remain in centered alignment in the bone tunnel because tensioning imparts an equal distribution of axial force upon the graft. Central alignment of the graft in the bone tunnel fosters an equal distribution of axial forces and minimizes contact between bone, such as sharp bone at the edges of the bone tunnel, and the soft tissue of the graft, thus reducing the possibility of abrasion and tearing of the graft.

It should be understood that variations and modifications within the spirit and scope of the invention, beyond those discussed herein, may occur to those skilled in the art to which the invention pertains. Accordingly, all expedient modifications readily attainable by one versed in the art from the disclosure set forth herein are to be included as further embodiments of the present invention. The scope of the present invention accordingly is to be defined as set forth in the appended claims.

The invention claimed is:

1. A fixation device for securing one end of a graft to bone, said device comprising:
   an implant body having first and second ends, the first end having an opening configured to receive an insertion tool and the second end having a recess, wherein the recess is proximal to the opening; and
   a graft interface member having a graft holding portion and an implant coupling portion having a distal end and a proximal end, the distal end of the coupling portion comprises a snap-fit type connection that is configured to be received and held in the recess to permit the implant body to rotate independently of the graft interface member, the proximal end of the coupling portion is configured to be operably associated with the graft holding portion;
   wherein the graft holding portion has a central longitudinal axis and is configured and adapted to hold a graft aligned with the central longitudinal axis.

2. The fixation device according to claim 1 wherein the graft holding portion comprises an enclosed loop.

3. The fixation device according to claim 1 wherein the graft holding portion comprises a cage.

4. The fixation device according to claim 3 wherein the cage comprises a cage bottom portion and a cage top portion attachable to the cage bottom portion.

5. The fixation device according to claim 4 wherein the cage top portion comprises at least one detent configured and adapted to attach the cage top portion to the cage bottom portion.

6. The fixation device according to claim 5 wherein the cage bottom portion has at least one fitting configured and adapted to receive the detent.

7. The fixation device according to claim 4 wherein the cage has at least one wall portion and at least one opening through the at least one wall portion.

8. The fixation device according to claim 7 wherein the at least one wall portion has an interior surface comprising serrations.

9. The fixation device according to claim 3 wherein the cage comprises at least one longitudinal wall section and a circular end wall segment.

10. The fixation device according to claim 9 wherein the at least one longitudinal wall section has at least one opening.

11. The fixation device according to claim 1 wherein the graft holding portion comprises a helical screw portion.

12. The fixation device according to claim 1 wherein the implant coupling portion comprises a flexible post.

13. The fixation device according to claim 12 wherein the flexible post has a flared tip portion.

14. The fixation device according to claim 13 wherein the flared tip portion is slotted.

15. The fixation device according to claim 1 wherein the recess in the second opposed end of the implant body has an undercut section.

16. The fixation device according to claim 1 wherein implant body and the graft interface member are integrally connected to each other.

17. The fixation device according to claim 1 wherein the opening in the first opposed end of the implant body is hexagonal.

18. The fixation device according to claim 17 wherein the hexagonal opening in the first opposed end of the implant body tapers to an internally threaded portion.

19. The fixation device according to claim 1 wherein the opening in the first opposed end of the implant body includes an internally threaded portion.

20. The fixation device according to claim 1 wherein the implant body has an outer surface at least a portion of which contains threads for implantation into bone.

21. The fixation device of claim 1, wherein the implant coupling portion is received in the recess from the second end of the implant.

22. The fixation device of claim 1, wherein the graft holding portion comprises a cage having at least two separate members.

23. The fixation device of claim 22, wherein the cage has a first member and a second member, the first and second members being configured and dimensioned to mate.

24. A fixation device for securing one end of a graft to bone, said device comprising:
- an implant body having first and second ends, the first end having an opening configured and adapted to receive an insertion tool and the second end having a recess, wherein the opening and the recess are not in communication with each other; and
- a graft interface member having a graft holding portion and an implant coupling portion, at least a portion of the coupling portion is configured and adapted to be received in the recess to permit the implant body to rotate independently of the graft interface member;
- wherein the implant coupling portion comprises a snap-fit type connection;
- wherein the graft holding portion has a central longitudinal axis and is configured and adapted to hold a graft aligned with the central longitudinal axis.

* * * * *